United States Patent [19]

Berger et al.

[11] Patent Number: 5,189,041
[45] Date of Patent: Feb. 23, 1993

[54] TRICYCLIC 5-HT₃ RECEPTOR ANTAGONISTS

[75] Inventors: Jacob Berger, Los Altos Hills; Robin D. Clark, Palo Alto, both of Calif.

[73] Assignee: Syntex (U.S.A.) Inc., Palo Alto, Calif.

[21] Appl. No.: 614,326

[22] Filed: Nov. 16, 1990

[51] Int. Cl.$^5$ .................. A61K 31/44; C07D 471/02; C07D 233/00

[52] U.S. Cl. .................... 514/288; 514/214; 514/305; 514/213; 514/291; 514/292; 514/299; 540/484; 540/552; 546/86; 546/89; 546/66

[58] Field of Search ........... 514/288, 214, 305, 291, 514/292, 299, 286; 546/66, 86, 89; 540/552, 484

[56] References Cited

U.S. PATENT DOCUMENTS

| | | | |
|---|---|---|---|
| 4,218,453 | 8/1980 | Hannart | 546/66 |
| 5,013,733 | 5/1991 | Coates et al. | 514/213 |

FOREIGN PATENT DOCUMENTS

| | | |
|---|---|---|
| 0261964 | 3/1988 | European Pat. Off. |
| 0306323 | 3/1989 | European Pat. Off. |
| 0356098 | 2/1990 | European Pat. Off. |
| 0377238 | 7/1990 | European Pat. Off. |
| 0385722 | 9/1990 | European Pat. Off. |
| 0392663 | 10/1990 | European Pat. Off. |
| 3810552A1 | 10/1989 | Fed. Rep. of Germany . |
| 2121394 | 8/1972 | France . |
| 2290878 | 3/1989 | Japan . |
| WO84/00166 | 1/1984 | PCT Int'l Appl. . |
| 8803801 | 6/1988 | PCT Int'l Appl. . |
| 2068731 | 8/1981 | United Kingdom ...... 514/288 |

OTHER PUBLICATIONS

*The Lancet*, Sep. 23, 1989, p. 717.
*J. Pharmacol. Exp. Ther.*, 1988, 245, 773.
*Trends Pharmacol. Sci.*, 1988, 9, 141.
*Gastroenterology Clinics of North America*, 1989, 18, 437.

Primary Examiner—Richard L. Raymond
Assistant Examiner—Shailendra Kumar
Attorney, Agent, or Firm—Wayne W. Montgomery; Derek P. Freyberg; Tom M. Moran

[57] ABSTRACT

5-HT₃ receptor antagonist compounds of the formula

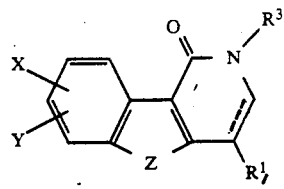

in which Z is —O—, —S— or —N(R²)—; R¹ and R² are independently selected from hydrogen and lower alkyl or are together —(CH₂)$_n$— wherein n is 2 to 4; and R³ is selected from

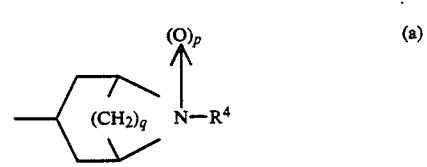

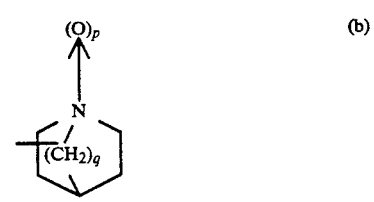

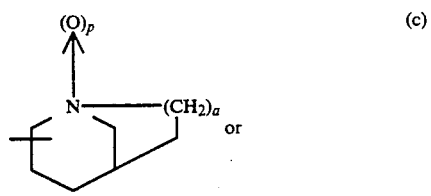

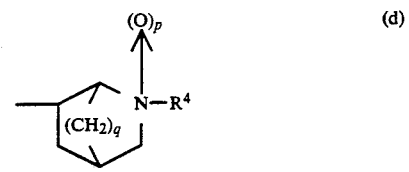

and the pharmaceutically acceptable salts, individual isomers, compositions, and methods of use thereof.

43 Claims, No Drawings

TRICYCLIC 5-HT₃ RECEPTOR ANTAGONISTS

FIELD OF THE INVENTION

This invention relates to novel compounds which are 5-HT$_3$ receptor antagonists, to pharmaceutical compositions containing them and to methods for their use and preparation. The invention also relates to novel intermediates useful in the synthesis of such compounds.

BACKGROUND OF THE INVENTION

Serotonin, a neurotransmitter with mixed and complex pharmacological characteristics, was first discovered in 1948 and subsequently has been the subject of an immense quantity of research. Serotonin, also referred to as 5-hydroxytryptamine (5-HT), acts both centrally and peripherally on discrete 5-HT receptors. Current dogma delineates 5-HT receptors into three major sub-classifications—5-HT$_1$, 5-HT$_2$ and 5-HT$_3$—each of which may also be heterogeneous. Receptors of the 5-HT$_3$ subclass pervade autonomic neurons and appear to regulate the release of a variety of neurotransmitters in the gastrointestinal, cardiovascular and central nervous systems.

5-HT$_3$ receptors are located in high densities on neurons associated with the emetic reflex and drugs which block the interactions of serotonin at the 5-HT$_3$ receptor level, i.e., 5-HT$_3$ receptor antagonists, possess potent antiemetic properties. Such antagonists demonstrate utility for counteracting the emetic effects of cancer chemotherapy and radiotherapy (see Drugs Acting on 5-Hydroxytryptamine Receptors: *The Lancet* Sep. 23, 1989 and refs. cited therein.).

Functional bowel disorders are prevalent in much of the industrialized world. Chronic gastroesophageal reflux disease alone may be present in as much as 15% of the population. Use of prokinetic agents is one of the most effective methods known for treating such disorders. Because many 5-HT$_3$ antagonists possess prokinetic properties and are relatively free from side effects they are particularly useful in the treatment of gastrointestinal diseases (see Reynolds R. C. Prokinetic Agents: A Key in the Future of Gastroenterology. *Gastroenterology Clinics of North America* 1989; 18: 437–457).

5-HT$_3$ receptors are present in those areas of the brain which control mood, emotion, reward and memory. 5-HT$_3$ receptor antagonists reduce mesolimbic dopamine levels, a necessary property for antipsychotic activity. Such antagonists also increase cholinergic tone in the limbic-cortical region, which may explain their cognitive enhancing effects. In addition, 5-HT$_3$ antagonists possess anxiolytic properties, demonstrate potential for use in the treatment of dependency disorders and are under investigation in patients with schizophrenia (see article from *The Lancet* previously cited).

There is evidence that 5-HT$_3$ receptors mediate nociceptive input to afferent neurons (see Glaum, S., Proudfit, H. K., and Anderson, E. G. 1988; *Neurosci. Lett.* 95, 313). 5-HT$_3$ antagonists may therefore be of value in the control of pain, particularly migraine (see Peatfield R. 1988; Drugs and the Treatment of Migraine: *Trends. Pharmacol. Sci.* 9: 141).

The 5-HT$_3$ receptor antagonist ICS 205-930 inhibits arrhythmias in a variety of animal models and exerts mixed class III and class I antiarrhythmic properties in ventricular myocytes (see Scholtysik, G., Imoto, Y., Yatani, A. and Brown, A. M. 1988; *J. Pharmacol. Exp. Ther.* 245, 773 and reference therein). 5-HT$_3$ antagonists may therefore be of use in treating or preventing arrhythmias.

The disclosure of these and the documents referred to throughout this application are incorporated herein by reference.

SUMMARY OF THE INVENTION

The first aspect of this invention is a compound of Formula I:

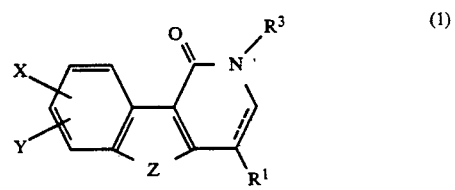

(1)

in which:
the dashed line denotes an optional bond;

X and Y are independently selected from hydrogen, halogen, hydroxy, lower alkoxy, lower alkyl, nitro, amino, aminocarbonyl, (lower alkyl)amino, di(lower alkyl)amino, and (lower alkanoyl)amino;

Z is —O—, —S— or —N(R$^2$)—;

R$^1$ and R$^2$ are independently selected from hydrogen and lower alkyl or are together —(CH$_2$)$_n$— wherein n is an integer from 2 to 4; and R$^3$ is selected from

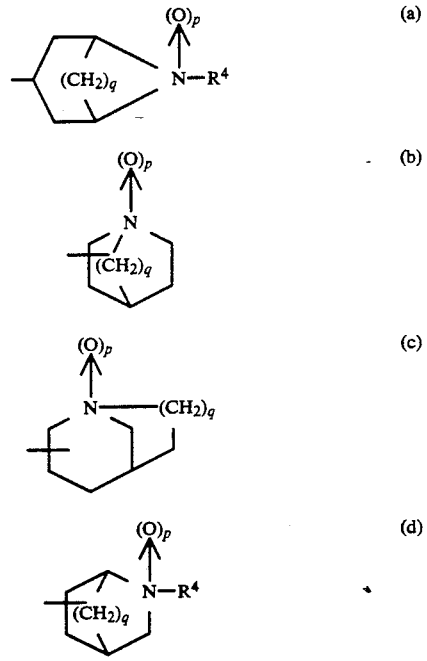

in which:
p is 0 or 1;
q is 1, 2, or 3; and

R$^4$ and C$_{1-7}$ alkyl, C$_{3-8}$ cycloalkyl, C$_{3-8}$ cycloalkyl-C$_{1-2}$ alkyl, or a group (CH$_2$)$_t$R$^5$ where t is 1 or 2 and R$^5$ is thienyl, pyrrolyl, or furyl, each optionally further substituted by one or two substituents selected from C$_{1-6}$ alkyl, C$_{1-6}$ alkoxy, trifluoromethyl or halogen, or is phenyl optionally substituted by one or two substituents selected from C$_{1-4}$ alkoxy, trifluoromethyl, halogen nitro, carboxy, esterified carboxy, and C$_{1-4}$ alkyl optionally substituted by hydroxy, $C_{1-4}$ alkoxy, carboxy, esterified carboxy or in vivo hydrolyzable acyloxy; their pharmaceutically acceptable salts and individual isomers or mixtures of isomers.

A second aspect of this invention is a pharmaceutical composition containing a compound of Formula I in admixture with one or more suitable excipients.

A third aspect of this invention is a method for treating diseases involving emesis, gastrointestinal disorders, CNS disorders, cardiovascular disorders or pain, particularly migraine, by administering a therapeutically effective amount of a compound of Formula I to a subject in need thereof.

A fourth aspect of this invention is a compound of Formula II which is useful as an intermediate in preparing a compound of Formula I:

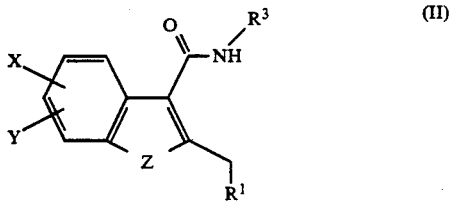

wherein X, Y, Z, $R^1$ and $R^3$ are as defined for Formula I.

A fifth aspect of this invention is the processes for preparing compounds of Formula I and is set forth in the "Detailed Description Of The Invention."

DETAILED DESCRIPTION OF THE INVENTION

Definitions

Unless otherwise stated, the following terms used in the specification and claims have the meanings given below:

"Active ingredient" means a pharmaceutically effective amount, as defined above, of a compound of Formula I.

"Alkyl" means a straight, branched, or cyclic saturated hydrocarbon radical having from one to the number of carbon atoms designated. For example $C_{1-7}$ alkyl is alkyl having at least one but no more than seven carbon atoms, e.g., methyl, ethyl, i-propyl, n-propyl, n-butyl, cyclopropylmethyl, pentyl, cyclohexyl, heptyl and the like.

"Animal" includes humans, non-human mammals (such as dogs, cats, rabbits, cattle, horses, sheep, goats, swine, and deer) and non-mammals such as birds and the like.

"Carboxy" means the carboxyl group —COOH.

"Cytotoxic agents" include platinum anti-cancer agents such as cisplatin (cis-diamminedichloroplatinum), as well as non-platinum anti-cancer drugs such as cyclophosphamide (cytoxin), vincristrine (leurocristine), procarbazine (N-(1-methylethyl)-4-[(2-methylhydrazino)methyl]-benzamide), methotrexate, fluorouracil, mechlorethamine hydrochloride (2-chloro-N-(2-chloroethyl)-N-methylethanamine hydrochloride), doxorubicin, adriamycin, dactinomycin (actinomycin-D), cytarabine, carmustine, dacarbazine, and others listed at page 1143 of the *Journal of Clinical Oncology* 1989; 7(8): 1143.

"Disease" specifically includes any unhealthy condition of an animal or part thereof and may be caused by, or incident to, medical or veterinary therapy applied to that animal, i.e., the "side effects" of such therapy. Thus, "disease" here includes the emesis caused by therapy with agents having emetogenic side effects, in particular by therapy for cancer, such as chemotherapy with cytotoxic agents and radiotherapy.

"Emesis", for the purposes of this application, will have a meaning that is broader than the normal, dictionary definition and includes not only vomiting, but also nausea and retching.

"Esterified carboxy" means the ester group —COOR wherein R is alkyl as defined above.

"Halogen" means fluorine, chlorine, bromine, or iodine. Preferred halogens are chlorine and bromine;

"In vivo hydrolyzable acyloxy" means a group —OC(O)R, wherein R is alkyl as defined above, capable of undergoing enzymatic hydrolysis within a living organism.

"Leaving group" includes halogen, methanesulfonyloxy (mesyloxy), ethanesulfonyloxy, benzenesulfonyloxy, p-toluenesulfonyloxy (tosyloxy), and the like.

"Lower alkyl" means an alkyl of one to six carbon atoms, i.e., $C_{1-6}$ alkyl.

"Lower alkoxy", "(lower alkyl)amino", "di(lower alkyl)amino", "(lower alkanoyl)amino", and similar terms mean alkoxy, alkylamino, dialkylamino, alkanoylamino, etc. in which the or each alkyl or alkanoyl radical contains from one to six carbon atoms.

"Optional" or "optionally" means that the subsequently described event or circumstance may or may not occur, and that the description includes instances where said event or circumstance occurs and instances in which it does not. For example, "optional bond" means that the bond may or may not be present and that the description includes both single bonds and double bonds; "Optionally followed by converting the free base to the acid addition salt" means that the conversion may or may not be carried out in order for the process described to fall within the invention, and the invention includes those processes wherein the free base is converted to the acid addition salt and those processes in which it is not.

"Pharmaceutically acceptable" means that which is useful in preparing a pharmaceutical composition that is generally safe and non-toxic and includes that which is acceptable for veterinary use as well as human pharmaceutical use.

"Pharmaceutically acceptable salts" means salts which possess the desired pharmacological activity and which are neither biologically nor otherwise undesirable. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclooct-2-[2.2.2]oct-2-ene-1-carboxylic acid, glucoheptonic acid, 4,4'-methylenebis(3-hydroxy-2-naphthoic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. In addition, pharmaceutically acceptable salts may be formed where hydroxy substituents are capable of forming salts with inorganic or organic bases. Acceptable inorganic bases include sodium hydroxide, sodium carbonate, potassium hydroxide, aluminum hydroxide and calcium hydroxide. Acceptable organic bases include diethanolamine, tromethamine, N-methylglucamine, ethanolamine, triethanolamine, and the like. Preferred pharmaceutically acceptable salts are those formed with hydrochloric acid.

"Pharmaceutically effective amount" means that amount which, when administered to an animal for treating a disease, is sufficient to effect such treatment, as defined above, for the disease.

"Treatment" means any treatment of a disease in an animal and includes:

(1) preventing the disease from occurring in an animal which may be predisposed to the disease but does not yet experience or display symptoms of the disease, (2) inhibiting the disease, i.e., arresting its development, or (3) relieving the disease, i.e., causing regression of the disease.

Compounds that have identical molecular formulae but differ in the nature or sequence of bonding of their atoms or in the arrangement of their atoms in space are termed "isomers". Isomers that differ in the nature or sequence of bonding of their atoms are termed "constitutional isomers". Isomers that differ only in the arrangement of their atoms in space are termed "stereoisomers". Stereoisomers that are not mirror images of one another are termed "diasteromers" and stereoisomers that are mirror images are termed "enantiomers" or sometimes "optical isomers". Stereoisomers that are superimposable upon their mirror images are termed "achiral" and those not superimposable are termed "chiral". A carbon atom bonded to four different groups is termed a "chiral center" or alternatively an "asymmetric carbon".

When a compound has a chiral center, a pair of enantiomers of opposite chirality is possible. An enantiomer may be characterized by the absolute configuration of its chiral center and described by the R- and S-sequencing rules of Cahn and Prelog (i.e., as (R)- and (S)-isomers) or by the manner in which the molecule rotates the plane of polarized light and designated as dextrorotatory or levorotatory (i.e., as (+)- and (−)-isomers, respectively). A compound may exist as either individual enantiomer or as a mixture thereof. A mixture containing equal proportions of the enantiomers is termed a "racemic mixture" or "racemate" and may be described as the (RS)- or (±)-mixture thereof. Unless indicated otherwise, the description or naming of a particular compound in the specification and claims is intended to include both individual enantiomers and mixtures, racemic or otherwise, thereof. Conventions for stereochemical nomenclature, methods for the determination of sterochemistry and the separation of stereoisomers are well-known in the art (see discussion in Chapter 4 of "Advanced Organic Chemistry", 3rd edition, March, Jerry, John Wiley and Sons, New York, 1985).

Certain compounds of Formulae I and II may exist as stereoisomers. For example, the $R^3$ substituent described herein may exhibit a chiral center at the ring carbon which is bonded to the amide nitrogen. In addition, compounds of Formula I wherein the optional bond is absent and $R^1$ is lower alkyl or $R^1$ and $R^2$ are together —$(CH_2)_n$— may exhibit a chiral center at the 4-position or the 3a-position, respectively. Finally, compounds of Formula I or II may exist as the endo or exo form in relation to the $R^3$ substituent.

When a compound of Formula I or II exhibits a chiral center, a pair of enantiomers exists. When two chiral centers are present in a compound of Formula I, four separate steroisomers exist (i.e., two separate pairs of enantiomers). When a compound of Formula I exhibits two chiral centers and may exist as endo or exo, eight separate stereoisomers are possible (i.e., two separate pairs of enantiomers in the endo or exo form).

It is to be understood that when referring to Formulae I and II or subformulae (b), (c) and (d) in this application, a straight line depicting the covalent bond between the asymmetric carbon and the amide nitrogen represents either the R or S configuration or a mixture, racemic or otherwise, thereof. Similarly, when referring to Formula I wherein the optional bond is absent, a straight line depicting the covalent bond between the assymetric carbon and the $R^1$ substituent represents either the R or S configuration or a mixture, racemic or otherwise, thereof. For purposes of the present application when referring to a compound by name or by formula and endo or exo is not designated, it is to be understood that the reference is to both forms.

Certain $R^3$ substituents described in this application are of particular interest and are therefore defined specifically. These $R^3$ substituents of particular interest are as follows:

(1) subformula (b) where q is 2 and p is 0 having the specific formula

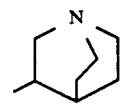

is referred to as 1-azabicyclo[2.2.2]oct-3-yl;

(2) subformula (b) where q is 2 and p is 0 having the specific formula

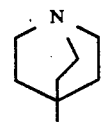

is referred to as 1-azabicyclo[2.2.2]oct-4-yl;

(3) subformula (a) where q is 3, p is 0 and $R^4$ is methyl having the specific formula

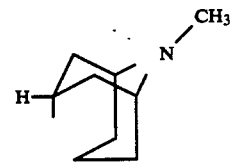

is referred to as endo-9-methyl-9-azabicyclo[3.3.1]non-3-yl;

(4) subformula (a) where q is 3, p is 0 and $R^4$ is methyl having the specific formula is referred to as exo-9-methyl-9-azabicyclo[3.3.1]non-3-yl;

(5) subformula (a) where q is 2, p is 0 and $R^4$ is methyl having the specific formula is referred to as endo-8-methyl-8-azabicyclo[3.2.1]oct-3-yl;

(6) subformula (a) where q is 2, p is 0 and $R^4$ is methyl having the specific formula is referred to as exo-8-methyl-8-azabicyclo[3.2.1]oct-3-yl;

(7) subformula (c) wherein q is 2 and p is 0 having the specific formula is referred to as endo-1-azabicyclo[3.3.1]non-4-yl; and (8) subformula (c) wherein q is 2 and p is 0 having the specific formula is referred to as exo-1-azabicyclo[3.3.1]non-4-yl.

Compounds of Formulae I and II are named in accordance with generally acceptable nomenclature rules established by "Chemical Abstracts" and numbered as shown below. For example, the compound of Formula I wherein the optional bond is present, each X, Y and $R^1$ is hydrogen and $R^3$ is 1-azabicyclo[2.2.2]oct-3-yl is named 2-(1-azabicyclo[2.2.2]oct-3-yl)-1,2-dihydro-5-methyl-1-oxopyrido[4.3-b]indole when Z is —N(CH₃)—;

2-(1-azabicyclo[2.2.2]oct-3-yl)-1,2-dihydro-1-oxopyrido[4.3-b]benzothiophene when Z is —S—; and 2-(1-azabicyclo[2.2.2]oct-3-yl)-1,2-dihydro-1-oxopyrido[4.3-b]benzofuran when Z is &13 O—.

The compound of Formula I wherein the optional bond is present, each X and Y is hydrogen, Z is —N(R²)—, $R^1$ and $R^2$ are together —(CH₂)₃— and R₃ is 1-azabicyclo[2.2.2]oct-3-yl is named 2-(1-azabicyclo[2.2.2]oct-3-yl)-2,4,5,6-tetrahydro-1-oxo-1H-indolo[3,2,1-ij][1,6]naphthyridine.

The compound of Formula II wherein each X, Y and $R^1$ is hydrogen and $R^3$ is 1-azabicyclo[2.2.2]oct-3-yl is named 3-[(1-azabicyclo[2.2.2]oct-3-yl)aminocarbonyl]-1,2-dimethylindole when Z is —N(CH₃)—;

3-[(1-azabicyclo[2.2.2]oct-3-yl)aminocarbonyl]-2-methylbenzothiophene when Z is —S—; and 3-[(1-azabicyclo[2.2.2]oct-3-yl)aminocarbonyl]-2-methylbenzofuran when Z is —O—.

Utility

Compounds of Formula I are 5-HT₃ receptor antagonists which exhibit utility for treating disease in animals, particularly humans. Examples of diseases that may be treated using the compounds of Formula I include emesis, gastrointestinal disorders, central nervous system (CNS) disorders, cardiovascular disorders and pain, particularly migraine.

The compounds of Formula I are useful in the treatment of emesis. Such emesis may be induced by or result from surgical anesthesia, motion (e.g., travel by air, car or ship), chemotherapy, radiotherapy and radiation poisoning. The compounds of Formula I are of particular value in treating (especially preventing) the emesis induced by radiation poisoning or radiotherapy or chemotherapy with cytotoxic agents.

The compounds of Formula I are useful in the treatment of gastrointestinal diseases, i.e., diseases of the stomach, esophagus and of both the large and small intestines. Examples of specific diseases include, but are not limited to, dyspepsia (e.g., non-ulcer dyspepsia), gastric stasis, peptic ulcer, reflux esophagitis, flatulence, bile reflux gastritis, pseudo-obstruction syndrome, irritable colon syndrome (which may result in chronic constipation and diarrhea), diverticular disease, biliary dysmotility (which may result in sphincter of Oddi dysfunction and "sludge" or microscopic crystals in the gall bladder), gastroparesis (e.g., diabetic, postsurgical or idiopathic), irritable bowel syndrome and retarded gastric emptying. The compounds of Formula I are also useful as short-term prokinetics to facilitate diagnostic radiology and intestinal intubation. In addition, the compounds are useful for treating diarrhea, particularly diarrhea induced by cholera and carcinoid syndrome.

The compounds of Formula I are useful in treating CNS diseases, i.e. diseases of the central nervous system. Categories of such diseases include cognitive disorders, psychoses, obsessive/compulsive and anxiety/depression behavior. Cognitive disorders include attentional or memory deficit, dementia states (including senile dementia of the Alzheimer's type and aging), cerebral vascular deficiency and Parkinson's disease. Psychoses that may be treated using the compounds of this invention include paranoia, schizophrenia and autism. Representative, treatable anxiety/depressive states include anticipatory anxiety (e.g., prior to surgery, dental work, etc.), depression, mania, convulsions and anxiety caused by withdrawal from addictive substances such as nicotine, alcohol, common narcotics, cocaine and other drugs of abuse.

Compounds of Formula I may be useful in the treatment of cardiovascular diseases. Such diseases may include arrhythmias and hypertension.

It is thought that 5-HT$_3$ antagonists prevent certain adverse nervous transmissions and/or prevent vasodilation and are therefore of value for reducing perceived levels of pain. Compounds of Formula I may, therefore, be useful in treating pain, particularly that associated with cluster headaches, migraines, trigeminal neuralgia and visceral pain (e.g., that caused by abnormal distension of hollow visceral organs).

In summary, an aspect of this invention is a method for treating an animal, particularly a human, exhibiting a disease involving emesis, a gastrointestinal disorder, a CNS disorder, a cardiovascular disorder or pain, particularly migraine, comprised of administering a therapeutically effective amount of a compound of Formula I to such animal.

Pharmacology

5-HT$_3$ receptor binding affinity may be determined by the Rat Cerebral Cortex Binding Assay, a predictive in vitro assay which assesses the binding affinity of a compound for the 5-HT$_3$ receptor. See methods described in Kilpatrick, G. J., Jones, B. J. and Tyers, M. B., *Nature* 1987: 330: 24–31. The assay, as adapted for testing compounds of Formula I, is set out in Example 8 of this application. The compounds of Formula I exhibit affinity for the 5-HT$_3$ receptor in this assay.

In vivo 5-HT$_3$ receptor antagonist activity may be determined by measuring inhibition of the von Bezold-Jarisch reflex in anesthetized rats, an accepted indicator of 5-HT$_3$ antagonist activity. See methods of Butler, A., Hill, J. M., Ireland, S. J., Jordan, C. C., Tylers, M. B., *Brit. J. Pharmacol.* 1988; 94: 397–412; Cohen, M. L., Bloomquist, W., Gidda, J. S., Lacefield, W., *J. Pharmacol. Exp. Ther.* 1989; 248: 197–201; and Fozard, J. R., MDL 72222: *Arch. Pharmacol.* 1984; 326: 36–44. The details of the procedure, as modified for testing the compounds Formula I, are set out in Example 9 of this application. Compounds of Formula I inhibit the von Bezold-Jarisch reflex.

Anti-emetic activity may be determined by measuring reduction of cisplatin-induced emesis in ferrets, an accepted test for determining anti-emetic activity in vivo. See methods by Costall, B., Domeney, A. M., Naylor, R. J., and Tattersall, F. D.. *Neuropharmacology* 1986; 25(8): 959–961; and Miner, W. D. and Sanger G. J., *Brit. J. Pharmacol.* 1986; 88: 497–499. A general description is set out in Example 10 of this application. Compounds of Formula I exhibit anti-emetic activity in this assay.

Anti-emetic activity may also be determined by measuring reduction of cisplatin-induced emesis in dogs. See methods described by Smith, W. L., Alphin, R. S., Jackson, C. B., and Sancilio, L. F., *J. Pharm. Pharmacol.* 1989; 41: 101–105; and Gylys, J. A., *Res. Commun. Chem. Pathol. Pharmacol.* 1979; 23(1): 61–68. A more detailed description, as modified for testing the compounds of Formula I, is set out in Example 11 of this application. Compounds of Formula I exhibit anti-emetic activity in this assay.

Gastrokinetic activity may be determined by measuring the rate of gastric emptying after oral administration of test meal to rats. See methods developed by Droppleman, D., Gregory, R., and Alphin, R. S., *J. Pharmacol. Methods* 1980; 4(3): 227–30. The procedures of Droppleman et al. are accepted methods for determining gastrointestinal activity in vivo. The gastrokinetic assay is detailed in Example 12 of this application. Compounds of Formula I exhibit gastrokinetic activity in this assay.

Anxiolytic activity is determined by the art-recognized Crawley and Goodwin two-compartment exploratory model as described in Kilfoil, T., Michel, A., Montgomery, D., and Whiting, R. L., *Neuropharmacology* 1989; 28(9): 901–905. In brief, the method involves determining whether a compound reduces the natural anxiety of mice in a novel, brightly lighted area. A detailed description is set forth in Example 13 of this application. Compounds of Formula I are active in this assay.

Cognition enhancing activity may be determined by the mouse habituation/cognitive enhancement test. See Procedures described in Barnes, J. M., Costall, B., Kelly, M. E., Naylor, F. J., Onaivi, E. S., Tomkins, D. M. and Tyers, M. B. *Br. J. Pharmacol.* 1989; 98: 693P. This procedure utilizes the exploratory model described above to test for improvements in the impaired cognitive performance of aged mice. A detailed description is set forth in Example 14 of this application.

Anxiolytic activity during withdrawal from drugs of abuse may be determined by the mouse light/dark withdrawal anxiety test. See methods described in Carboni, E., Acquas, E., Leone, P., Perezzani, L., and Di Chiara, G., *Eur. J. Pharmacol* 1988; 151: 159–160. This Procedure utilizes the exploratory model described above to test for anxiolytic activity after chronic administration and subsequent abrupt cessation of alcohol, cocaine or nicotine treatments. A detailed description is set forth in Example 15 of this application.

All of the aforementioned citations to in vitro and in vivo methods for determining activity of the compounds of this invention and other documents cited herein are incorporated herein by reference.

Administration and Pharmaceutical Composition

In general, compounds of Formula I will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. Therapeutically effective amounts of compounds of Formula I may range from approximately 1.0 nanogram per Kg (ng/Kg) body weight per day to 1.0 mg/Kg body weight per day. Preferably the amount will be approximately 10 ng/Kg/day to 0.1 mg/Kg/day. Therefore, a therapeutically effective amount for a 70 Kg human may range from 70 ng/day to 70 mg/day, preferably 700 ng/day to 7.0 mg/day.

One of ordinary skill in the art of treating such diseases will be able, without undue experimentation and in reliance upon personal knowledge and the disclosure of this application, to ascertain a theraputically effective amount of a compound of Formula I for a given disease.

Generally compounds of Formula I will be administered as pharmaceutical compositions either orally, systemically (e.g., transdermally, intranasally or by suppository) or parenterally (e.g., intramuscularly, intravenously or subcutaneously). Compositions can take the form of tablets, pills, capsules, semisolids, powders, sustained release formulations, solutions, suspensions, elixirs, aerosols, or any other appropriate composition and are, in general, comprised by the active ingredient in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the active ingredient in aerosol form. Inert gases suitable for this purpose are nitrogen, carbon dioxide, nitrous oxide, etc. Other suitable pharmaceutical carriers and their formulations are described in A. R. Alfonso 1990. *Remington's Pharmaceutical Science.* 18th ed. Easton, Pa.: Mack Publishing Company.

The amount of a compound of Formula I in the composition may vary widely depending upon the type of formulation, size of a unit dosage, kind of excipients and other factors known to those of skill in the art of pharmaceutical sciences. In general, the final composition will comprise about 0.000001% w to about 10.0% w of active ingredient with the remainder being the excipient or excipients. Preferably the level of active ingredient will be about 0.00001% w to about 1.0% w, with the remainder being a suitable excipient or excipients.

Preferably the pharmaceutical composition is administered in a single unit dosage form for continuous treatment or in a single unit dosage form ad libitum when relief of symptoms is specifically required.

PRESENTLY PREFERRED EMBODIMENTS

While the broadest definition of this invention is as set forth in the Summary of the Invention, certain embodiments are preferred. For example, favored compounds of Formula I are those wherein X and Y are independently selected from hydrogen or hydroxy, Z is —N(R$^2$)—, R$^1$ and R$^2$ are independently selected from hydrogen and lower alkyl or R$^1$ and R$^2$ are together —(CH$_2$)$_3$— and R$^3$ is 1-azabicyclo[2.2.2]oct-3-yl or 1-azabicyclo[2.2.2]oct-4-yl.

Of particular interest are those compounds of Formula I wherein X and Y are hydrogen, Z is —N(R$^2$)—, R$^1$ is hydrogen and R$^2$ is methyl or R$^1$ and R$^2$ together are —(CH$_2$)$_3$— and R$^3$ is 1-azabicyclo[2.2.2]oct-3-yl, specifically the S-enantiomers thereof. Representative compounds are made by following the procedures set out in Examples 1, 2, 3, 4 and 5.

It is understood that these subgroups of special interest are particularly useful in the pharmaceutical compositions and methods of treatment of this invention.

PROCESS FOR PREPARING COMPOUNDS OF THE INVENTION

Compounds of the Formula I may be prepared by the reaction sequence shown below

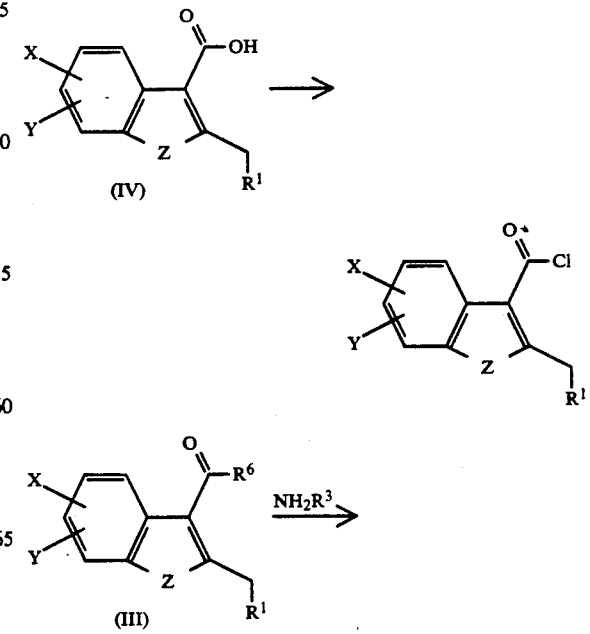

wherein $R^6$ is chloride or lower alkoxy, L is a leaving group and X, Y, Z, $R^1$ and $R^3$ are defined as in their broadest definitions set forth in the Summary of the Invention, with the processes applying particularly well to the presently preferred embodiments.

Scheme I

Presently, the preferred method of preparing compounds of Formula I is by a two step synthesis comprising (1) converting a compound of Formula III or IV to the corresponding substituted amide of Formula II and (2) reacting the amide with a formylating agent, e.g. a dialkylformamide, in the presence of a strong base and then acidifying (see Scheme I). Compounds of Formula I wherein the optional bond is absent may subsequently be prepared by reduction.

Step 1

Compounds of Formula II are prepared by converting a carboxylic acid of Formula IV to the corresponding acid chloride of Formula III and subsequently reacting the acid chloride with a substituted amine of the formula $NH_2R^3$ wherein $R^3$ is defined as in its broadest definition set forth in the Summary of the Invention. Alternatively, compounds of Formula II may be prepared by reacting an ester of Formula III with the substituted amine. Either reaction is carried out at 20° C. to 200° C. and ambient pressure for 0.5 to 3 hours in a suitable solvent. Representative, suitable solvents include dichloromethane, THF and toluene. A detailed description of Step 1 is set forth in Example 2 of this application.

In general, the starting materials utilized in the Preparation of compounds of Formula II are known to those of ordinary skill in the art. For example, the carboxylic acid of Formula IV wherein Z is —S— and $R^1$ is hydrogen, namely 2-methylbenzothiophene-3-carboxylic acid, may be prepared by reacting 2-methylbenzothiophene with acetyl chloride in the presence of stannic chloride to form 3-acetyl-2-methylbenzothiophene and wherein $R^6$ is chloride or lower alkoxy and X, Y, Z, $R^1$ and $R^3$ are defined as in their broadest definitions set forth in the Summary of the Invention, with the processes applying particularly well to the presently preferred embodiments.

PROCESS FOR PREPARING COMPOUNDS OF THE INVENTION

Scheme II

Compounds of Formula I may be prepared by the reaction sequence shown below subsequently converting this product to the carboxylic acid (J. Gubin, N. Claeys, E. Deray and M. DesCamps, *Eur. J. Med. Chem.-Chimica Therapeutica,* (1975) 10, 418–424).

The methyl ester of Formula III wherein Z is —N(R$^2$)— and R$^1$ and R$^2$ are together —(CH$_2$)$_3$—, namely methyl 6,7,8,9-tetrahydropyrido[1,2-a]indole-2-carboxylate, is prepared by reacting 6,7,8,9-tetrahydropyrido[1,2-a]indole with phosgene to form 1-chloroformyl-6,7,8,9-tetrahydropyrido[1,2-a]indole and subsequently converting this product to the methyl ester. A more detailed description of this procedure is set forth in Example 1 of this application. The 6,7,8,9-tetrahydropyrido[1,2-a]indole may be prepared via an intramolecular Wittig reaction (M. D. Crenshaw and H. Zimmer, *J. Heterocyclic Chem.,* (1984) 21, 623).

The carboxylic acid of Formula IV wherein Z is —O— and R$^1$ is hydrogen, namely 2-methylbenzofuran-3-carboxylic acid is prepared by the methylation of benzofuran-3-carboxylic acid (C. Chou and W. S. Trahanovsky, *J. Org. Chem.,* (1986) 51, 4208). The ethyl ester of Formula III wherein Z is —N(CH$_3$)— and R$^1$ is hydrogen, namely ethyl 1,2-dimethylindole-3-carboxylate, is prepared from ethyl acetoacetate N-methyl-N-phenyl-hydrazone (M. J. Kornet, A. P. Thio and L. M. Tolbert, *J. Org. Chem.,* (1980) 45, 30). The ethyl ester is subsequently converted to 1,2-dimethylindole-3-carboxylic acid by hydrolysis.

Substituted amines of the formula NH$_2$R$^3$ that are particularly useful in this step are those wherein R$^3$ is one of the following radicals:
1-azabicyclo[2.2.2]oct-3-yl;
1-azabicyclo[2.2.2]oct-4-yl;
endo-9-methyl-9-azabicyclo[3.3.1]non-3-yl;
exo-9-methyl-9-azabicyclo[3.3.1]non-3-yl;
endo-8-methyl-8-azabicyclo[3.2.1]oct-3-yl;
exo-8-methyl-8-azabicyclo[3.2.1]oct-3-yl;
endo-1-azabicyclo[3.3.1]non-4-yl; or
exo-1-azabicyclo[3.3.1]non-4-yl

Step 2

The compounds of Formula IA (compounds of Formula I wherein the optional bond is present) are prepared by reacting compounds of Formula II with a dialkylformamide in the presence of a strong base and than acidifying with aqueous hydrochloric acid. The reaction is carried out in a suitable solvent at temperatures ranging from −70° C. to 25° C. under an inert atmosphere (e.g., argon) and ambient pressure. Suitable solvents include diethyl ether, dimethoxyethane or tetrahydrofuran (THF). The dialkylformamide, preferably dimethyl formamide (DMF), is generally used in molar excess relative to the amide. Any readily available base, such as a Grignard reagent or an appropriate alkyllithium, preferably n-butyllithium, can be utilized. A detailed description of Step 2 is set forth in Example 3 of this application.

Compounds of Formula IB (compounds of Formula I wherein the optional bond is absent) may be prepared by reduction of the corresponding compound of Formula IA. The reduction is carried out under standard hydrogenation conditions with an appropriate hydrogenation catalyst and in a suitable polar, organic solvent. Reaction pressures may vary from atmospheric approximately 15 megapascals (MPa) and temperatures may range from ambient to approximately 100° C. While any standard catalyst (e.g., rhodium on alumina, etc.) may be used, certain catalysts are favored. Preferred catalysts include 10% palladium hydroxide, 20% palladium hydroxide on carbon, Pearlman's catalyst (50% H$_2$O—20% palladium content) and palladium/BaSO$_4$. Suitable solvents include ethanol, DMF, acetic acid, ethyl acetate, tetrahydrofuran, toluene, and the like.

Depending upon the catalyst, solvent, pressure and temperature chosen, the reduction process may take from a few hours to a few days to complete. As an example, a reaction carried out with 20% palladium hydroxide in acetic acid and 70% perchloric acid at 350 KPa and 85° C. takes approximately 24 hours for full reduction to occur. A detailed description of the reduction of a compound of Formula IA is set forth in Example 4 of this application.

A compound of Formula IA may be reduced in either the free base or salt form. When reducing a salt of a compound of Formula I, wherein R$^1$ is lower alkyl or R$^1$ and R$^2$ are together —(CH$_2$)$_n$—, and an optically active reagent is employed to form the salt, formation of one enantiomer over the other may be favored at the 4-position or the 3a-position, respectively. Preferred salts are those formed from hydrochloric acid, hydrobromic acid, camphorsulfonic acid and acetic acid.

Scheme II

Alternatively, compounds of Formula I may be prepared by a three step synthesis comprising (1) converting a compound of Formula III to the corresponding unsubstituted amide, (2) reacting the amide with a formylating agent in the presence of a strong base and then acidifying, followed by (3) condensation with an appropriate alkylating agent (see Scheme II).

Step 1

Compounds of Formula VI may be prepared by proceeding as in Step 1 of Scheme I but replacing the substituted amine with ammonia.

Step 2

Compounds of Formula VA (compounds of Formula V wherein the optional bond is present) may be prepared by proceeding as in Step 2 of Scheme I but substituting a compound of Formula VI for the compound of Formula II. Compounds of Formula VB (compounds of Formula V wherein the optional bond is absent) may be prepared by proceeding as described above for the hydrogenation of a compound of Formula IA but substituting a compound of Formula VA.

Step 3

Compounds of Formula I may be prepared by reacting, in the presence of a strong base, a compound of Formula V with an alkylating agent of the formula R$^3$L wherein R$^3$ is defined as in its broadest definition set forth in the Summary of the Invention and L is a leaving group such as halogen, mesyloxy, ethanesulfonyloxy, benzenesulfonyloxy, or tosyloxy. The reaction is carried out under standard amide alkylating conditions (Luh, T. and Fung S. H., Synth. Commun. (1979), 9, 757) in an inert solvent at a reaction temperature of 20° C. to 100° C. Appropriate bases include sodium or sodium hydride and are usually employed in molar excess. Suitable solvents include N,N-dialkylformamides, such as N,N-dimethylformamide, or tetrahydrofuran.

Alternatively, alkylation may be accomplished via phase-transfer catalyst (PTC) techniques. Such techniques comprise carrying out the reaction in the presence of catalyst and in a liquid-liquid two phase solvent system (Gajda, T. and Zwierzak, A., Synthesis, Communications (1981), 1005), or preferably, in a solid-liquid system (Yamawaki, J., Ando, T. and Hanafusa, T., Chem, Lett. (1981), 1143; Koziara, A., Zawaszki, S. and Zwierzak, A., Synthesis (1979) 527, 549.)

A liquid-liquid two-phase system is comprised of an aqueous phase consisting of a concentrated alkali hydroxide solution (e.g., 50% aqueous sodium hydroxide), a nonpolar phase comprised of an inert solvent, and an appropriate catalyst. A solid-liquid system consists of a powdered alkali hydroxide/alkali carbonate suspended in a nonpolar inert solvent and catalyst.

The reaction is effected by adding slowly to a PTC system containing a compound of Formula V an alkylating agent of the formula $R^3Br$ until 10 to 50% in excess. The reaction mixture is kept at reflux until the reaction is complete. The mixture is then cooled to room temperature and the compound of Formula I is isolated by conventional methods. Suitable nonpolar solvents include benzene, toluene, and the like. Appropriate catalysts include tetra-n-butyl-ammonium hydrogen sulfate, alumina coated with potassium fluoride, and tricaprylylmethylammonium chloride.

Alkylating agents of the formula $R^3L$ that are particularly useful in this step are those wherein $R^3$ is one of the following radicals:
1-azabicyclo[2.2.2]oct-3-yl;
1-azabicyclo[2.2 2]oct-4-yl;
endo-9-methyl-9-azabicyclo[3.3.1]non-3-yl;
exo-9-methyl-9-azabicyclo[3.3.1]non-3-yl;
endo-8-methyl-8-azabicyclo[3.2.1]oct-3-yl;
exo-8-methyl-8-azabicyclo[3.2.1]oct-3-yl;
endo-1-azabicyclo[3.3.1]non-4-yl; or
exo-1-azabicyclo[3.3.1]non-4-yl.

ADDITIONAL PROCESSES

Compounds of Formula I wherein substituents X and/or Y are $NH_2$ may be prepared by the reduction of a corresponding nitro substituent; wherein X and/or Y are alkoxy or dialkylamino, by substitution of a corresponding nitro or halo substituent; or wherein X and/or Y is hydroxy, by the reduction of a corresponding alkoxy substituent. Furthermore, compounds of Formula I wherein Y is Cl, Br, I or $NO_2$ may be prepared by the introduction of such substituent onto a ring activated by a X substituent such as $NH_2$, NR, OH or alkoxy; or wherein X and/or Y is an acetamido substituent, by the acylation of a corresponding amino substituent. A detailed description of the preparation of a compound of Formula I wherein X is hydroxy is set forth in Example 5 of this application.

Compounds of Formula I wherein p is 1 (compounds of Formula I wherein the cyclic amine portion of $R^3$ is in the N-oxide form) may be prepared by oxidation of the corresponding compound of Formula I wherein p is 0, preferably the free base form. The oxidation is carried out at a reaction temperature of approximately 0° C. with an appropriate oxidizing agent and in a suitable inert, organic solvent. Suitable oxidizing agents include trifluoroperacetic acid, permaleic acid, perbenzoic acid, peracetic acid, and m-chloroperoxybenzoic acid. Suitable solvents include halogenated hydrocarbons, e.g., dichloromethane. A detailed description of this procedure is set forth in Example 6 of this application. Alternatively, the compounds of Formula I wherein p is 1 may be prepared using N-oxide derivatives of the starting materials or intermediates.

Compounds of Formula I wherein p is 0 (compounds of Formula I wherein the cyclic amine portion of $R^3$ is not in the N-oxide form) may be prepared by reduction of the corresponding compound of Formula I wherein p is 1. The reduction is carried out under standard conditions with an appropriate reducing agent in a suitable solvent. The mixture is occasionally agitated while the reaction temperature is gradually increased over a range of 0° C. to 80° C. Appropriate reducing agents include sulfur, sulfur dioxide, triaryl phosphines (e.g., triphenyl phosphine), alkali boranates (e.g., lithium, sodium boranate, etc.), phosphorous trichloride and tribromide. Suitable solvents include acetonitrite, ethanol or aqueous diozane.

As will be apparent to one of skill in the art, compounds of Formula I may be prepared as individual optical isomers or as mixtures, racemic or otherwise, thereof. For example, the individual enantiomers of a compound of Formula I may be prepared by reacting the racemic mixture with an optically active resolving agent to form a pair of diastereomeric compounds. Diastereomers have distinct physical properties (e.g., melting points, boiling points, solubilities, reactivity, etc.) and can be readily separated by taking advantage of these dissimilarities. For example, the diastereomers may be separated by chromatography or, preferably, by separation/resolution techniques based upon differences in solubility. The optically pure enantiomer is than recovered, along with the resolving agent, by any practical means that would not result in racemization.

While resolution of enantiomers may be carried out using covalent diastereomeric derivatives of compounds of Formula I, dissociable complexes are preferred, e.g., crystalline diastereomeric salts. Such crystalline diastereomeric salts may be prepared by using an optically active acid as the resolving agent. Suitable resolving acids include tartaric acid, o-nitrotartranilic acid, mandelic acid, malic acid, the 2-arylpropionic acids in general, and camphorsulfonic acid.

Individual enantiomers of compounds of Formula I may also be separated by such methods as direct or selective crystallization or by any other method known to one of ordinary skill in the art. A more detailed description of the techniques applicable to the resolution of stereoisomers of compounds of Formula I can be found in Jean Jacques, Andre Collet, Samuel H. Wilen 1981. Enanriomers, Racemates and Resolutions. John Wiley & Sons, Inc. Alternatively, individual isomers of compounds of Formula I may be prepared using optically active starting materials or intermediates.

As will be apparent to one of skill in the art, compounds of Formula I may be prepared as individual diastereomers. For example, a compound of Formula I wherein the optional bond is absent, $R^1$ is lower alkyl or $R^1$ and $R^2$ are together —$(CH_2)_n$— and $R^3$ may exist as either endo or exo, four separate enantiomeric pairs are possible (i.e., the (R,R)(S,S)-endo-, (R,R)(S,S)-exo-, (R,S)(S,R)-endo- and (R,S)(S,R)-exo-racemates). The enantiomers of each pair, relative to those of the other pairs, are diastereomers (i.e., nonsuperimposable stereoisomers).

Once the diastereomers are separated into enantiomeric pairs, the pure enantiomers may be resolved by any of the techniques described above. Alternatively, individual isomers of compounds of Formula I may be prepared using stereoisomeric forms of the starting materials or intermediates.

Compounds of Formula I may be converted to the corresponding acid addition salt with a pharmaceutically acceptable inorganic or organic acid. In addition, compounds of Formula I wherein X and/or Y hydroxy substituents form salts may be prepared with a pharmaceutically acceptable inorganic or organic base. Inorganic and organic acids and bases suitable for the preparation of the pharmaceutically acceptable salts of compounds of Formula I are set forth in the definitions section of this application.

Compounds of Formula I in the acid addition salt form may be converted to the corresponding free base by treatment with a suitable base such as ammonium hydroxide solution, sodium hydroxide or the like. Compounds of Formula I wherein X and/or Y hydroxy substituents form salts may be converted to the corresponding free base by treatment with a suitable acid such as hydrochloric acid.

In summary, the processes for preparing the compounds of Formula I are (1) converting an optionally substituted carboxylic acid of Formula IV to the corresponding acid chloride;

(2) reacting an optionally substituted carboxylic acid chloride or carboxylate ester of Formula III with a substituted amine of the formula $NH_2R^3$ to form a compound of Formula II;

(3) reacting an optionally substituted compound of Formula II with a dialkylformamide in the presence of a strong base and then acidifying to form a compound of Formula IA;

(4) optionally hydrogenating a compound of Formula IA to form a compound of Formula IB;

(5) reacting an optionally substituted carboxylic acid chloride or carboxylate ester of Formula III with ammonia to form a compound of Formula VI;

(6) reacting an optionally substituted compound of Formula VI with a dialkylformamide in the presence of a strong base and then acidifying to form a compound of Formula VA;

(7) optionally hydrogenating a compound of Formula VA to form a compound of Formula VB;

(8) reacting an optionally substituted compound of Formula V with an alkylating agent of the formula $R^3L$ to form a compound of Formula I;

(9) optionally reacting with or exchanging substituents present on a compound of Formula I to form an additional substituted compound of Formula I;

(10) optionally converting the acid salt of a compound of Formula I to the corresponding pharmaceutically acceptable free base;

(11) optionally converting the free base of a compound of Formula I to the corresponding pharmaceutically acceptable salt;

(12) optionally oxidizing a compound of Formula I wherein p is 0 to the corresponding N-oxide wherein p is 1;

(13) optionally reducing the N-oxide of a compound of Formula I wherein p is 1 to the corresponding compound of Formula I wherein p is 0; or

(14) optionally separating a mixture of isomers of a compound of Formula I into a single isomer.

In any of the above processes, a reference to Formula I, II, III, IV, V or VI refers to such Formula wherein X, Y, Z, $R^1$, $R^2$, $R^3$, $R^4$, $R^5$, $R^6$, n, p, q and t are as defined in heir broadest definitions set forth in the Summary of the Invention, with the processes applying particularly well to the Presently preferred embodiments.

EXAMPLE 1

Methyl 6,7,8,9-tetrahydropyrido[1,2-a]indole-1-carboxylate

The following is the preparation of a compound of Formula III in which

X and Y are hydrogen;

Z is —$N(R^2)$—; and $R^1$ and $R^2$ are together —$(CH_2)_3$—.

6,7,8,9-tetrahydropyrido[1,2-a]indole (1.15 g, 6.7 mmol) in methylene chloride (5 ml) was added dropwise at 0° C. to a solution of phosgene (10 mmol) in toluene (5 ml). The reaction mixture was stirred for one hour after which methanol (1 ml) was added gradually and the mixture allowed to warm to ambient temperature. The solvent was removed under reduced pressure to yield a white solid. Recrystallization from hexane afforded 1.08 g (70.3% of methyl 6,7,8,9-tetrahydropyrido[1,2-a]indole-1-carboxylate, as white crystals, m.p. 102°–103° C. Anal. for $C_{14}H_{15}NO_2$: Calcd. C, 73.34; H, 6.59; N, 6.11. Found: C, 72.96; H, 6.61; N, 6.33.

EXAMPLE 2

3-[(1-azabicyclo[2.2.2]oct-3-yl)aminocarbonyl]-1,2-dimethylindole

The following is the Preparation of a compound of Formula II in which

X and Y are hydrogen;

$R^1$ is hydrogen;

Z is —$N(CH_3)$—; and $R^3$ is 1-azabicyclo[2.2.2]oct-3-yl.

Method A (S)-3-[(1-Azabicyclo[2.2.2]oct-3-yl)aminocarbonyl]-1,2-dimethylindole 1,2-dimethylindole-3-carboxylic acid (1.05 g, 5.5 mmol) was dissolved with oxalyl chloride (0.55 ml, 6 mmol) and dimethylformamide (0.1 ml) in dichloromethane (30 ml) and stirred at room temperature for one hour. The mixture was then concentrated under reduced pressure, and the residue was dissolved in dichloromethane (20 ml). The resulting mixture was added dropwise at 0° C. to a solution of (S)-3-amino-1-azabicyclo[2.2.2]octane (0.7 g, 5.5 mmol) in dichloromethane (10 ml). The solution was stirred at room temperature for 30 minutes, after which the solvent was removed under vacuum. The residue was dissolved in water and washed with ethyl acetate. The aqueous layer was made basic with 10N aqueous sodium hydroxide, filtered and extracted with ethyl acetate. The organic layer was dried with anhydrous potassium carbonate, filtered, and then evaporated. Recrystallization from ethyl acetate afforded 0.7 g (46% yield) (S)-3-[(1-azabicyclo[2.2.2]oct-3-yl)aminocarbonyl]-1,2-dimethylindole, m.p. 176°–177° C.; $[\alpha]_D^{25}$ −51.90 (c 0.92, CHCl₃). Anal. for $C_{18}H_{23}N_3O$: Calcd: C, 72.70; H, 7.79; N, 14.13. Found: C, 72.75; H, 7.89; N, 14.15.

Proceeding as in Example 2, Method A, but replacing (S)-3-amino-1-azabicyclo[2.2.2]octane with (R)-3-amino-1-azabicyclo[2.2.2]octane there was prepared (R)-3-[(1-azabicyclo[2.2.2]oct-3-yl)aminocarbonyl]-1,2-dimethylindole, m.p. 174°–175° C.; $[\alpha]_D^{25}$ +50.5° (c 0.41, CHCl₃).

Proceeding as in Example 2, Method A, but replacing (S)-3-amino-1-azabicyclo[2.2.2]octane with (RS)-3-amino-1-azabicyclo[2.2.2]octane there was prepared (RS)-3-[(1-azabicyclo[2.2.2]oct-3-yl)aminocarbonyl]-1,2-dimethylindole, m.p. 165°-166° C.

Proceeding as in Example 2, Method A, but replacing (S)-3-amino-1-azabicyclo[2.2.2]octane with (RS)-3-amino-1-azabicyclo[2.2.2]octane and 1,2-dimethylindole-3-carboxylic acid with 2-methylbenzothiophene-3-carboxylic acid, there was prepared (RS)-3-[(1-azabicyclo[2.2.2]oct-3-yl)aminocarbonyl]-2-methylbenzothiophene, m.p. 207°-208° C.

Proceeding as in Example 2, Method A, but replacing (S)-3-amino-1-azabicyclo[2.2.2]octane with (RS)-3-amino-1-azabicyclo[2.2.2]octane and 1,2-dimethylindole-3-carboxylic acid with 2-methylbenzofuran-3-carboxylic acid there was prepared (RS)-3-[(1-azabicyclo[2.2.2]oct-3-yl)aminocarbonyl]-2-methylbenzofuran, m.p. 154°-155° C.

Proceeding as in Example 2, Method A, but replacing (S)-3-amino-1-azabicyclo[2.2.2]octane with endo-3-amino-9-methyl-9-azabicyclo[3.3.1]nonane there was prepared 3-[(endo-9-methyl-9-azabicyclo[3.3.1]non-3-yl)aminocarbonyl]-1,2-dimethylindole, m.p. 196° C.

Similarly proceeding as in Example 2, Method A, compounds of Formula II that may be prepared include:
3-[(1-azabicyclo[2.2.2]oct-4-yl)aminocarbonyl]-1,2-dimethylindole;
3-[(exo-9-methyl-9-azabicyclo[3.3.1]non-3-yl)aminocarbonyl]-1,2-dimethylindole;
3-[(endo-8-methyl-8-azabicyclo[3.2.1]oct-3-yl)aminocarbonyl]-1,2-dimethylindole;
3-[(exo-8-methyl-8-azabicyclo[3.2.1]oct-3-yl)aminocarbonyl]-1,2-dimethylindole;
3-[(endo-1-azabicyclo[3.3.1]non-4-yl)aminocarbonyl]-1,2-dimethylindole;
3-[(exo-1-azabicyclo[3.3.1]non-4-yl)aminocarbonyl]-1,2-dimethylindole;
3-[(1-azabicyclo[2.2.2]oct-4-yl)aminocarbonyl]-2-methylbenzothiophene;
3-[(endo-9-methyl-9-azabicyclo[3.3.1]non-3-yl)aminocarbonyl]-2-methylbenzothiophene;
3-[(exo-9-methyl-9-azabicyclo[3.3.1]non-3-yl)aminocarbonyl]-2-methylbenzothiophene;
3-[(endo-8-methyl-8-azabicyclo[3.2.1]oct-3-yl)aminocarbonyl]-2-methylbenzothiophene;
3-[(exo-8-methyl-8-azabicyclo[3.2.1]oct-3-yl)aminocarbonyl]-2-methylbenzothiophene;
3-[(endo-1-azabicyclo[3.3.1]non-4-yl)aminocarbonyl]-2-methylbenzothiophene;
3-[(exo-1-azabicyclo[3.3.1]non-4-yl)aminocarbonyl]-2-methylbenzothiophene;
3-[(1-azabicyclo(2.2.2)oct-4-yl)aminocarbonyl]-2-methylbenzofuran;
3-[(endo-9-methyl-9-azabicyclo[3.3.1]non-3-yl)aminocarbonyl]-2-methylbenzofuran;
3-[(exo-9-methyl-9-azabicyclo[3.3.1]non-3-yl)aminocarbonyl]-2-methylbenzofuran;
3-[(endo-8-methyl-8-azabicyclo[3.2.1]oct-3-yl)aminocarbonyl]-2-methylbenzofuran;
3-[(exo-8-methyl-8-azabicyclo[3.2.1]oct-3-yl)aminocarbonyl]-2-methylbenzofuran;
3-[(endo-1-azabicyclo[3.3.1]non-4-yl)aminocarbonyl]-2-methylbenzofuran; and
3-[(exo-1-azabicyclo[3.3.1]non-4-yl)aminocarbonyl]-2-methylbenzofuran.

Method B (RS)-3-[(1-azabicyclo[2.2.2]oct-3-yl)aminocarbonyl]-1,2-dimethylindole (RS)-3-amino-1-azabicyclo[2.2.2]octane (0.14 g, 1.1 mmol) in toluene (2 ml) was mixed dropwise into a solution of trimethylaluminum (1.1 mmol) in toluene (1 ml), in a manner so that the temperature of the mixture did not exceed 10° C. The mixture was stirred for 30 minutes, after which a solution of ethyl 1,2-dimethylindole-3-carboxylate (0.22 g; 1 mmol) in toluene (2 ml) was added. The reaction mixture was heated under reflux for 3 hours, then cooled, and added at 0° C. to aqueous hydrochloric acid (10% 5 ml). After separation of the layers, the aqueous layer was made basic with 10N aqueous sodium hydroxide, filtered, and extracted with ethyl acetate. The organic layer was dried with anhydrous potassium carbonate, filtered and evaporated to afford 0 12 g (40% yield) of crude product. A sample was recrystallized from ethyl acetate to yield (RS)-3-[(1-azabicyclo[2.2.2]oct-3-yl) aminocarbonyl]-1,2-dimethylindole, m.p. 165°-166° C.

Proceeding as in Example 2, Method B, but replacing (RS)-3-amino-1-azabicyclo[2.2.2]octane with (S)-3-amino-1-azabicyclo[2.2.2]octane and ethyl 1,2-dimethylindole-3-carboxylate with ethyl 1,2-dimethyl-5-methoxyindole-3-carboxylate there was prepared (S)-5-methoxy-3-[(1-azabicyclo[2.2.2]oct-3-yl)aminocarbonyl]-1,2-dimethylindole, m.p. 171°-172° C., $[\alpha]_D^{25}$ −44.8° (c 0.63, CHCl$_3$). Anal. for C$_{19}$H$_{25}$N$_3$O$_2$: Calcd.: C, 69.70; H, 7.70; N, 12.83. Found: C, 69.34; H, 7.68; N, 12.52.

Proceeding as in Example 2, Method B, but replacing (RS)-3-amino-1-azabicyclo[2.2.2]octane with (S)-3-amino-1-azabicyclo[2.2.2]octane and ethyl 1,2-dimethylindole-3-carboxylate with methyl 6,7,8,9-tetrahydropyrido[1,2-a]indole-1-carboxylate, from Example 1, there was prepared (S)-1-[(1-azabicyclo[2.2.2]oct-3-yl)aminocarbonyl]-6,7,8,9-tetrahydropyrido[1,2-a]indole (82% yield), m.p. 163°-164° C.

Proceeding as in Example 2, Method B, but replacing (RS)-3-amino-1-azabicyclo[2.2.2]octane with (RS)-endo-3-amino-1-azabicyclo[3.3.1]nonane there was prepared (RS)-endo-3-[(1-azabicyclo[3.3.1]non-4-yl)aminocarbonyl]-1,2-dimethylindole.

Proceeding as in Example 2, Method B, compounds of Formula II that may be prepared include:
3-[(1-azabicyclo[2.2.2]oct-4-yl)aminocarbonyl]-1,2-dimethylindole;
3-[(endo-9-methyl-9-azabicyclo[3.3.1]non-3-yl)aminocarbonyl]-1,2-dimethylindole;
3-[(exo-9-methyl-9-azabicyclo[3.3.1]non-3-yl)aminocarbonyl]-1,2-dimethylindole;
3-[(endo-8-methyl-8-azabicyclo[3.2.1]oct-3-yl)aminocarbonyl]-1,2-dimethylindole;
3-[(exo-8-methyl-8-azabicyclo[3.2.1]oct-3-yl)aminocarbonyl]-1,2-dimethylindole;
3-[(exo-1-azabicyclo[3.3.1]non-4-yl)aminocarbonyl]-1,2-dimethylindole;
3-[(1-azabicyclo[2.2.2]oct-4-yl)aminocarbonyl]-2-methylbenzothiophene;
3-[(endo-9-methyl-9-azabicyclo[3.3.1]non-3-yl)aminocarbonyl]-2-methylbenzothiophene;
3-[(exo-9-methyl-9-azabicyclo[3.3.1]non-3-yl)aminocarbonyl]-2-methylbenzothiophene;

3-[(endo-8-methyl-8-azabicyclo[3.2.1]oct-3-yl)aminocarbonyl]-2-methylbenzothiophene;
3-[(exo-8-methyl-8-azabicyclo[3.2.1]oct-3-yl)aminocarbonyl]-2-methylbenzothiophene;
3-[(endo-1-azabicyclo[3.3.1]non-4-yl)aminocarbonyl]-2-methylbenzothiophene;
3-[(exo-1-azabicyclo[3.3.1]non-4-yl)aminocarbonyl]-2-methylbenzothiophene;
3-[(1-azabicyclo[2.2.2]oct-4-yl)aminocarbonyl]-2-methylbenzofuran;
3-[(endo-9-methyl-9-azabicyclo[3.3.1]non-3-yl)aminocarbonyl]-2-methylbenzofuran;
3-[(exo-9-methyl-9-azabicyclo[3.3.1]non-3-yl)aminocarbonyl]-2-methylbenzofuran;
3-[(endo-8-methyl-8-azabicyclo[3.2.1]oct-3-yl)aminocarbonyl]-2-methylbenzofuran;
3-[(exo-8-methyl-8-azabicyclo[3.2.1]oct-3-yl)aminocarbonyl]-2-methylbenzofuran;
3-[(endo-I-azabicyclo[3.3.1]non-4-yl)aminocarbonyl]-2-methylbenzofuran;
3-[(exo-1-azabicyclo[3.3.1]non-4-yl)aminocarbonyl]-2-methylbenzofuran;

EXAMPLE 3

(S)-2-(1-azabicyclo[2.2.2]oct-3-yl)-1,2-dihydro-5-methyl-1-oxopyrido[4,3-b]indole The following is the preparation of a compound of Formula I in which
the optional bond is present;
X and Y are hydrogen;
$R^1$ is hydrogen;
Z is —N(CH$_3$)—; and
$R^3$ is 1-azabicyclo[2.2.2]oct-3-yl.

(S)-3-[(1-azabicyclo[2.2.2]oct-3-yl)aminocarbonyl]-1,2-dimethylindole (0.67 g, 2.2 mmol), from Method A of Example 2, was dissolved in dry tetrahydrofuran (20 ml). The indole solution was maintained at −70° C. while a solution of n-butyllithium in hexane (5 mmol) was added dropwise. The reaction mixture was stirred at −10° C. for an hour and then cooled again to −70° C., after which dimethylformamide (0.5 ml) was added in one portion. The reaction mixture was allowed to warm to room temperature over 1.5 hours, then cooled to 0° C. and acidified with 10% aqueous hydrochloric acid. The layers were separated and the aqueous layer was washed with ethyl acetate. The aqueous layer was then made basic with 10N aqueous sodium hydroxide and extracted with ethyl acetate. The ethylacetate extract was dried over anhydrous sodium sulfate, filtered and then evaporated to afford 0.47 g (68% yield) of a white solid. A sample of the solid was recrystallized from ethyl acetate to yield (S)-2-(1-azabicyclo[2.2.2]oct-3-yl)-1,2-dihydro-5-methyl-1-oxo-5H-pyrido[4,3-b]indole, m.p. 251°-252° C., $[\alpha]_D^{25}$ +50.5° (c=0.5; CHCl$_3$). The hydrochloride salt was prepared from ethanol-HCl to yield (S)-2-(1-azabicyclo[2.2.2]oct-3-yl)-1,2-dihydro-5-methyl-1-oxopyrido[4,3-b]indole hydrochloride, m.p 254°-255° C.; $[\alpha]_D^{25}$ −67.1° (c 0.32, H$_2$O).

Proceeding as in Example 3, but replacing (S)-3-[(1-azabicyclo[2.2.2]oct-3-yl)aminocarbonyl]-1,2-dimethylindole with (R)-3-[(1-azabicyclo[2.2.2]oct-3-yl)aminocarbonyl]-1,2-dimethylindole, from Method A of Example 2, there were prepared (R)-2-(1-azabicyclo[2.2.2]oct-3-yl)-1,2-dihydro-5-methyl-1-oxopyrido[4,3-b]indole (99% yield), m.p. 250°-251° C. −60.2° (c 0.47, CHCl$_3$) and (R)-2-(1-azabicyclo[2.2.-2]oct-3-yl)-1,2-dihydro-5-methyl-1-oxopyrido[4,3-b]indole hydrochloride, m.p. 252°-253° C., $[\alpha]_D^{25}$ +66.2° (c 0.28, H$_2$O).

Proceeding as in Example 3, but replacing (S)-3-[(1-azabicyclo[2.2.2]oct-3-yl)aminocarbonyl]-1,2-dimethylindole with (RS)-3-[(1-azabicyclo[2.2.2]oct-3-yl)aminocarbonyl]-1,2-dimethylindole, from Method A of Example 2, there were prepared (RS)-2-(1-azabicyclo[2.2.2]oct-3-yl)-1,2-dihydro-5-methyl-1-oxopyrido[4,3-b]indole, m.p. 224°-224.5° C. and (RS)-2-(1-azabicyclo[2.2.2]oct-3-yl)-1,2-dihydro-5-methyl-1oxopyrido[4,3-b]indole hydrochloride, m.p. 258°-260° C.

Proceeding as in Example 3, but replacing (S)-3-[(1-azabicyclo[2.2.2]oct-3-yl)aminocarbonyl]-1,2-dimethylindole with (RS)-3-[(1-azabicyclo[2.2.2]oct-3-yl)aminocarbonyl]-2-methylbenzothiophene, from Method A of Example 2, there was prepared (RS)-2-(1-azabicyclo[2.2.2]oct-3-yl)-1,2-dihydro-1-Oxopyrido[4,3-b]benzothiophene hydrochloride (20% yield), m.p. >270° C.

Proceeding as in Example 3, but replacing (S)-3-[(1-azabicyclo[2.2.2]oct-3-yl)aminocarbonyl]-1,2-dimethylindole with (RS)-3-[(1-azabicyclo[2.2.2]oct-3-yl)aminocarbonyl]-2-methylbenzofuran, from Method A of Example 2, there was prepared (RS)-2-(1-azabicyclo[2.2.2]oct-3-yl)-1,2-dihydro-1-oxopyrido[4,3-b]benzofuran hydrochloride (8% yield), m.p. >270° C.

Proceeding as in Example 3, but replacing (S)-3-[(1-azabicyclo[2.2.2]oct-3-yl)aminocarbonyl]-1,2-dimethylindole with (S)-1-[(1-azabicyclo[2.2.2]oct-3-yl)aminocarbonyl]-6,7,8,9-tetrahydropyrido[1,2-a]indole, from Method B of Example 2, there was prepared (S)-2-(1-azabicyclo[2.2.2]oct-3-yl)-2,4,5,6-tetrahydro-1-oxo-1H-indole[3,2,1-ij][1,6]naphthyridine (27% yield), m.p. 256°-259° C., $[\alpha]_D^{25}$ −14.7° (c 0.25, H$_2$O).

Proceeding as in Example 3, but replacing (S)-3-[(1-azabicyclo[2.2.2]oct-3-yl)aminocarbonyl]-1,2-dimethylindole with (S)-3-[(1-azabicyclo[2.2.2]oct-3-yl)aminocarbonyl]-5-methoxy-1,2-dimethylindole, from Method B of Example 2, there was prepared (RS)-2-(1-azabicyclo[2.2.2]oct-3-yl)-1,2-dihydro-8-methoxy-5-methyl-1-oxopyrido[4,3-b]indole hydrochloride, m.p. 267°-268° C., $[\alpha]_D^{25}$ −57° (c 1.0, H$_2$O).

Proceeding as in Example 3, but replacing (S)-3-[(1-azabicyclo[2.2.2]oct-3-yl)aminocarbonyl]-1,2-dimethylindole with 3-[(endo-9-methyl-9-azabicyclo[3.3.1]-non-3-yl)aminocarbonyl]-1,2-dimethylindole, from Method A of Example 2, there was prepared 2-(endo-9-methyl-9-azabicyclo[3.3.1]non-3-yl)-1,2-dihydro-5-methyl-1-oxopyrido[4,3-b]indole hydrochloride, m.p. 331°-333° C.

Proceeding as in Example 3, but replacing (S)-3-[(1-azabicyclo[2.2.2]oct-3-yl)aminocarbonyl]-1,2-dimethylindole with (RS)-3-[(endo-1-azabicyclo[3.3.1]non-4-yl)aminocarbonyl]-1,2-dimethylindole, from Method B of Example 2, there was prepared (RS)-2-(endo-1-azabicyclo[3.3.1]non-4-yl)-1,2-dihydro-5-methyl-1-oxopyrido[4,3-b]indole hydrochloride, m.p. >360° C.

Similarly proceeding as in Example 3 compounds of Formula I that may be prepared include:
2-(1-azabicyclo[2.2.2]oct-4-yl)-1,2-dihydro-5-methyl-1-oxo-5H-pyrido[4,3-b]indole;
2-(exo-9-methyl-9-azabicyclo[3.3.1]non-3-yl)-1,2-dihydro-5-methyl-1-oxopyrido[4,3-b]indole;
2-(endo-8-methyl-8-azabicyclo[3.2.1]oct-3-yl)-1,2-dihydro-5-methyl-1-oxopyrido[4,3-b]indole;
2-(exo-8-methyl-8-azabicyclo[3.2.1]oct-3-yl)-1,2-dihydro-5-methyl-1-oxopyrido[4,3-b]indole;

2-(exo-1-azabicyclo[3.3.1]non-4-yl)-1,2-dihydro-5-methyl-1-oxopyrido[4,3-b]indole;
2-(1-azabicyclo[2.2.2]oct-4-yl)-1,2-dihydro-1-oxopyrido[4,3-b]benzothiophene;
2-(endo-9-methyl-9-azabicyclo[3.3.1]non-3-yl)-1,2-dihydro-1-oxopyrido[4,3-b]benzothiophene;
2-(exo-9-methyl-9-azabicyclo[3.3.1]non-3-yl)-1,2-dihydro-1-oxopyrido[4,3-b]benzothiophene;
2-(endo-8-methyl-8-azabicyclo[3.2.1]oct-3-yl)-1,2-dihydro-1-oxopyrido[4,3-b]benzothiophene;
2-(exo-8-methyl-8-azabicyclo[3.2.1]oct-3-yl)-1,2-dihydro-1-oxopyrido[4,3-b]benzothiophene;
2-(endo-1-azabicyclo[3.3.1]non-4-yl)-1,2-dihydro-1-oxopyrido[4,3-b]benzothiophene;
2-(exo-1-azabicyclo[3.3.1]non-4-yl)-1,2-dihydro-1-oxopyrido[4,3-b]benzothiophene;
2-(1-azabicyclo[2.2.2]oct-4-yl)-1,2-dihydro-1-oxopyrido[4,3-b]benzofuran;
2-(endo-9-methyl-9-azabicyclo[3.3.1]non-3-yl)-1,2-dihydro-1-oxopyrido[4,3-b]benzofuran;
2-(exo-9-methyl-9-azabicyclo[3.3.1]non-3-yl)-1,2-dihydro-1-oxopyrido[4,3-b]benzofuran;
2-(endo-8-methyl-8-azabicyclo[3.2.1]oct-3-yl)-1,2-dihydro-1-oxopyrido[4,3-b]benzofuran;
2-(exo-8-methyl-8-azabicyclo[3.2.1]oct-3-yl)-1,2-dihydro-1-oxopyrido[4,3-b]benzofuran;
2-(endo-1-azabicyclo[3.3.1]non-4-yl)-1,2-dihydro-1-oxopyrido[4,3-b]benzofuran;
2-(exo-1-azabicyclo[3.3.1]non-4-yl)-1,2-dihydro-1-oxopyrido[4,3-b]benzofuran;
2-(1-azabicyclo[2.2.2]oct-4-yl)-2,4,5,6-tetrahydro-1-oxo-1H-indolo[3,2,1-ij][1,6]naphthyridine;
2-(endo-9methyl-9-azabicyclo[3.3.19 non-3yl)-2,4,5,6-tetrahydro-1-oxo-1H-indolo[3,2,1-ij][1,6]naphthyridine;
2-(exo-9-methyl-9-azabicyclo[3.3.1]non-3-yl)-2,4,5,6-tetrahydro-1-oxo-1H-indolo[3,2,1-ij][1,6]naphthyridine;
2-(endo-8methyl-8-azabicyclo[3.2.1]oct-3yl)-2,4,5,6-tetrahydro-1-oxo-1H-indolo[3,2,1-ij][1,6]naphthyridine;
2-(exo-8-methyl-8-azabicyclo[3.2.1]oct-3-yl)-2,4,5,6-tetrahydro-1-oxo-1H-indolo[3,2,1-ij][1,6]naphthyridine;
2-(endo-1-azabicyclo[3.3.1]non-4-yl)-2,4,5,6-tetrahydro-1-oxo-1H-indolo[3,2,1-ij][1,6]naphthyridine;
2-(exo-1-azabicyclo[3.3.1]non-4-yl)-2,4,5,6-tetrahydro-1-oxo-1H-indolo[3,2,1-ij][1,6]naphthyridine;

EXAMPLE 4

(RS)-2-(1-azabicyclo[2.2.2]oct-3-yl)-1,2,3,4-tetrahydro-5-methyl-1-oxopyrido[4,3-b]indole The following is the preparation of a compound of Formula I in which
the optional bond is not present;
X and Y are hydrogen;
$R^1$ is hydrogen;
Z is —N(CH$_3$)—; and
$R^3$ is 1-azabicyclo[2.2.2]oct-3-yl.

(RS)-2-(1-azabicyclo[2.2.2]oct-3-yl)-1,2-dihydro-5-methyl-1-oxopyrido[4,3-b]indole hydrochloride (0.3 g, 0.98 mmol), from Example 3, in acetic acid (5 ml, containing 3 drops of 70% perchloric acid) was reduced with 20% palladium hydroxide on carbon (0.1 g) at 80° C. and 350 kPa for 20 hours. The catalyst was removed by filtration and the filtrate was concentrated under reduced pressure. The residue was dissolved in water (10 ml), basified with ammonium hydroxide solution and extracted with ethyl acetate. The ethyl acetate was dried over anhydrous potassium carbonate, filtered and evaporated. The residue was purified by column chromatography (10% methanol in dichloromethane +1% ammonium hydroxide; silica; Rf. 0.3) to afford 0.5 g (16% yield) of (RS)-2-(1-azabicyclo[2.2.2]oct-3-yl)-1,2,3,4-tetrahydro-5-methyl-1-oxopyrido[4,3-b]indole.

The hydrochloride salt was prepared from ethanol-HCl to yield (RS)-2-(1-azabicyclo[2.2.2]oct-3-yl)-1,2,3,4-tetrahydro-5-methyl-1-oxopyrido[4,3-b]indole hydrochloride, m.p. >270°.

EXAMPLE 5

(S)-2-(1-azabicyclo[2.2.2]oct-3-yl)-1,2-dihydro-8-hydroxy-5-methyl-1-oxopyrido[4,3-b]indole The following is the preparation of a compound of Formula I in which
the optional bond is present;
X is hydroxy in the 8-position;
Y is hydrogen;
$R^1$ is hydrogen;
Z is —N(CH$_3$)—; and
$R^3$ is 1-azabicyclo[2.2.2]oct-3-yl.

A solution of BBr$_3$ (0.5 mmol) in dichloromethane (0.5 ml) was added dropwise at −70° C. to a solution of (S)-2-(1-azabicyclo[2.2.2]oct-3-yl)-1,2-dihydro-8-methoxy-5-methyl-1-oxopyrido[4,3-b]indole (0.11 g, 0.33 mmol) in dichloromethane (1 ml), from Example 3. The reaction mixture was warmed to ambient temperature, then recooled to −70° C. Methanol (0.5 ml) was added and the reaction mixture was brought to ambient temperature. The solvent was removed under reduced pressure and the residue was recrystallized from isopropanol to afford 0.04 g (37% yield) of (S)-2-(1-azabicyclo[2.2.2]oct-3-yl)-1,2-dihydro-8-hydroxy-5-methyl-1-oxopyrido[4,3-b]indole hydrobromide, m.p. 235°–250° C.

Proceeding as in Example 5 other compounds of Formula I wherein the optional bond is absent can be prepared.

EXAMPLE 6

(S)-2-(1-azabicyclo[2.2.2]oct-3-yl)-1,2-dihydro-5-methyl-1-oxopyrido[4,3-b]indole N-oxide The following is the preparation of a compound of Formula I in which
p is 1;
the optional bond is present;
X and Y are hydrogen;
$R^1$ is hydrogen;
Z is —N(CH$_3$)—; and
2]oct-3-yl.
$R^3$ is 1-azabicyclo[2.2.2]oct-3-yl.

m-Chloroperoxybenzoic acid (1.2 g, 7.0 mmol) was added in small portions at 0° C. to a solution of (S)-2-(1-azabicyclo[2.2.2]oct-3-yl)1,2-dihydro-5-methyl-1-oxopyrido[4,3-b]indole (1.8 g, 5.8 mmol), from Example 3, in dichloromethane (50 mL). The reaction mixture was stirred for additional 0.5 hour at 0° C. The solvent was removed under reduced pressure and the residue was purified by column chromatography (10% methanol in dichloromethane and 1% ammonium hydroxide) to afford 0.75 g (62% yield) of (S)-2-(1-azabicyclo[2.2.2]oct-3-yl)-1,2-dihydro-5-methyl-1-oxopyrido[4,3-b]indole N-oxide, as an amorphous solid, m.p 98°–102° C.

Proceeding as in Example 6 other compounds of Formula I wherein p is 1 can be prepared.

EXAMPLE 7

The following are representative pharmaceutical formulations containing a compound of Formula I.

Oral Formulation

A representative solution for oral administration contains:

| | |
|---|---|
| Active Ingredient | 100-1000 mg |
| Citric Acid Mono hydrate | 105 mg |
| Sodium Hydroxide | 18 mg |
| Flavouring | q.s. |
| Water | to 100 ml |

Intravenous Formulation

A representative solution for intravenous administration contains:

| | |
|---|---|
| Active Ingredient | 10-100 mg |
| Dextrose Monohydrate | q.s. to make isotonic |
| Citric Acid Monohydrate | 1.05 mg |
| Sodium Hydroxide | 0.18 mg |
| Water for Injection | to 1.0 ml |

Tablet Formulation

A representative tablet form of a compound of Formula I may contain:

| | |
|---|---|
| Active Ingredient | 5% |
| Microcrystalline cellulose | 69% |
| Stearic Acid | 25% |
| Colloidal Silica | 1% |

Example B

5-HT$_3$ Receptor Screening Assay

The following describes an in vitro assay for determining the 5-HT$_3$ receptor binding affinity of compounds of Formula I. The method is essentially that described by Kilpatrick et al., previously cited, which measures the affinity for 5-HT$_3$ receptors of the rat cerebral cortex radiolabelled with [$^3$H]quipazine.

Membranes are prepared from the cerebral cortices of rat brains homogenized in 50 mM Tris buffer (pH 7.4 at 4° C.) using a Polytron P10 tissue disrupter (setting 10, 2×10 sec bursts). The homogenate is centrifuged at 48,000×g for 12 min and the pellet obtained is washed, by resuspension and centrifugation, three times in homogenizing buffer. The tissue pellets are resuspended in the assay buffer, and are stored under liquid nitrogen until required.

The binding assays are conducted using a Tris-Krebs assay buffer of the following composition (mM): NaCl, 154; KCl, 5.4; KH$_2$PO$_4$, 1.2; CaCl$_2$.2H$_2$O, 2.5; MgCl$_2$, 1.0; glucose, 11; Tris, 10. Assays are conducted at 25° C. at 7.4 in a final volume of 0.25 ml. Zacopride (1.0 μM) is used to define the non-specific binding (NSB). 5-HT$_3$ receptors present in rat cortical membranes are labelled using 0.3-0.7 nM [$^3$H]quipazine (specific activity 50-66 Ci/mmol; New England Nuclear) in the presence of 0.1 μM paroxetine to prevent [$^3$H]quipazine binding to 5-HT uptake sites. The rat cortex membranes are incubated with [$^3$H]quipazine in the presence of 10 different concentrations of test compound ranging from $1 \times 10^{-12}$ to $1 \times 10^{-4}$ molar. Incubations are conducted for 45 min at 25° C. and are terminated by vacuum filtration over Whatman GF/B glass fiber filters using a Brandel 48 well cell harvester. After filtration the filters are washed for 8 sec with 0.1M NaCl. The filters are pretreated with 0.3% polyethyleneimine 18 hr prior to use in order to reduce filter binding of the radioligand. Radioactivity retained on the filters is determined by liquid scintillation counting.

The concentration of test compound producing 50% inhibition of radioligand binding is determined by an iterative curve fitting procedure. Affinities are expressed as the negative logarithm of the IC$_{50}$ value (pIC$_{50}$). Compounds of Formula I exhibit 5-HT$_3$ receptor binding affinity, i.e., pIC$_{50}$ values greater than 6.

EXAMPLE 9

5-HT$_3$ Antagonist Activity in Rats (Von Bezold-Jarisch Reflex)

The following describes an in vivo method for determining the 5-HT$_3$ antagonist activity of compounds of Formula I. The method is a modified version of that described by Butler et al., Cohen et al., and Fozard, all previously cited, in which the 5-HT$_3$ selective agonist 2-methyl-5-hydroxytryptamine (2-m-5-HT) is substituted for 5-HT.

Male Sprague-Dawley rats, 250-380 grams, are anesthetized with urethane (1.4 g/kg, i.p.). A tracheotomy is performed and a tube is inserted into the trachea to facilitate respiration. Jugular and femoral veins are canulated for intravenous administration of drug. The duodenum is canulated for intraduodenal administration of drug. Heart rate is monitored by Gould ECG/Biotech amplifiers. After at least a 30 min equilibration period and prior to administration of test compound, control responses to intravenous administration of 2-m-5-HT are determined and a minimal dose producing sufficient and consistent bradycardia is chosen.

Potency

Intravenous challenges to 2-m-5-HT are administered every 12 minutes. Either vehicle or test compound is administered intravenously 5 minutes before each challenge to 2-m-5-HT. Each successive administration of test compound is increased in dosage until responses to 2-m-5-HT are blocked.

Duration

Vehicle or test compound is administered intravenously or intraduodenally and subsequent challenges to 2-m-5-HT are administered at 5, 15, 30, 60, 120, 180, 240, 300 and, in some instances, 360, 420 and 480 minutes post dose.

For both potency and duration studies heart rate (beats/min) is recorded continuously for the duration of the study. Responses to 2-m-5-HT are represented by the peak decrease in heart rate. Effects of test compounds are represented as percent inhibition of the bradycardia induced by 2-m-5-HT. Data are analyzed by a one-way repeated measures ANOVA and followed by pairwise comparison to vehicle control using Fisher's LSD strategy. From a dose-response curve so constructed, an ID$_{50}$ value is obtained to represent the dose that inhibited 50% of the bradycardia induced by 2-m-5HT.

Compounds of Formula I exhibit 5-HT$_3$ receptor antagonist activity in this assay, i.e., ID$_{50}$ values less than 3.0 mg/kg, i.v.

EXAMPLE 10

Cisplatin-Induced Emesis in Ferrets

The following describes the procedure for determining the intravenous (i.v.) effects of compounds of Formula I on cisplatin-induced emesis in ferrets.

Adult, male, castrated ferrets are allowed food and water ad libitum both prior to and throughout the testing period. Each animal is randomly chosen and anesthetized with a metofane/oxygen mixture, weighed and assigned to one of three test groups. While anesthetized an incision is made along the ventral cervical region approximately two to four centimeters in length. The jugular vein is then isolated and cannulated with a capped saline filled PE-50 polyethylene tubing. The cannula is exteriorized at the base of the skull and the incision closed with wound clips. The animals are then returned to their cages and allowed to recover from anesthesia prior to commencement of the study.

Vehicle or test compound is administered i.v. at 1.0 ml/kg and 1.0 mg/kg, respectively. Within 2.0 minutes of the administration of vehicle or test compound, cisplatin is injected i.v. at 10 mg/kg. The animals are then observed continuously for a 5 hour period and emetic responses (i.e., vomiting and/or retching) are recorded. For purposes of this example and that of Example 11, vomiting is defined as the successful evacuation of stomach contents and a single episode of retching is defined as rapid and successive efforts to vomit occurring within a one minute time period.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

Intravenously administered compounds of Formula I are anti-emetic in this assay.

Proceeding as in Example 10 but administering the test compounds by oral route, the anti-emetic effects of compounds of Formula I may be evaluated. Orally administered compounds of Formula I are anti-emetic in this assay.

EXAMPLE 11

Cisplatin-Induced Emesis in Dogs

The following describes the procedure for determining the intravenous (i.v.) effects of compounds of Formula I on cisplatin-induced emesis in dogs.

Male and female dogs (6–15 kg) are fed one cup of dry dog food. One hour following feeding, cisplatin (cis-diamminedichloroplatinum) is administered i.v. at 3 mg/kg. Sixty minutes after the administration of cisplatin, either vehicle or test compound is injected i.v. at 0.1 ml/kg and 1.0 mg/kg, respectively. The dogs are then observed continuously for a 5 hour period and the emetic responses (i.e., vomiting and/or retching) are recorded.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

Compounds of Formula I exhibit anti-emetic activity in this assay.

Example 12

Gastric Emptying of Test Meal in Rats

The following describes an in vivo method of determining the gastrointestinal activity of the compounds of Formula I by measuring the rate of gastric emptying of test meal in rats. The method is that described by Droppleman et al., previously cited.

Test meal is prepared by slowly adding 20 grams of cellulose gum (Hercules Inc., Wilmington, Delaware) to 200 ml of cold distilled water that is being mixed in a Waring blender at approximately 20,000 rpm. Mixing continues until complete dispersion and hydration of the cellulose gum takes place (approximately 5 min). Three beef bouillon cubes are dissolved in 100 ml of warm water and then blended into the cellulose solution followed by 16 g of purified casein (Sigma Chemical Co., St. Louis, Mo.), 8 g of powdered confectioners sugar, 8 g of cornstarch, and 1 g of powdered charcoal. Each ingredient is added slowly and mixed thoroughly resulting in approximately 325 ml of a dark gray to black, homogenous paste. The meal is then refrigerated overnight during which time trapped air escapes. Prior to the assay the meal is removed from the refrigerator and allowed to warm to room temperature.

Mature male Sprague-Dawley rats (170 to 204 g) are deprived of food for 24 hours with water ad libitum. On the morning of the study each animal is weighed and randomly assigned to treatment groups consisting of ten animals per group. Each rat receives either vehicle, test compound or the reference standard metoclopramide by intraperitoneal injection. At 0.5 hours post injection 3.0 ml of test meal is orally administered to each rat with a 5.0 ml disposable syringe. Five test meal samples are weighed on an analytical balance and these weights are averaged to find a mean test meal weight. At 1.5 hours post injection each rat is sacrificed by carbon dioxide asphyxiation and the stomach is removed by opening the abdomen and carefully clamping and cutting the esophagus just below the pyloric sphincter. Taking care not to lose any of the its contents, each stomach is placed on a small, pre-weighed and correspondingly labeled 7 ml weigh boat and immediately weighed on an analytical balance. Each stomach is then cut open along the lesser curvature, rinsed with tap water, gently blotted dry to remove excess moisture and weighed. The amount of test meal remaining in the stomach is represented by the difference between the weight of the full stomach and the weight of the stomach empty. The difference between the amount of test meal remaining and the mean test meal weight represents the quantity of test meal that empties during the 1.5 hour post injection period.

Responses are represented as grams of meal emptied or percent change from control. Means and standard deviations of the test groups are compared to those of the reference groups. Significance is determined via Dunnett's t-test (Statistical Association Journal, December 1955; 1096-112).

Compounds of Formula I exhibit prokinetic activity in this assay.

EXAMPLE 13

The Mouse Anxiolytic Behaviour Model

The following describes an in vivo method for determining the anxiolytic activity of compounds of Formula I.

Naive male C5BI/6J mice, 18–20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin (1980), as described in Kilfoil et al., cited previously. Briefly, the chamber consists of a plexiglass box (44×21×21 cm), divided into two chambers by a black plexiglass partition. The partition dividing the two chambers contains a 13×5 cm opening through which the mouse can easily pass. The dark chamber has clear sides and a white floor marked with grids. A fluorescent tube light (40 watt) placed above the chambers provides the only illumination. The Digiscan Animal Activity Monitor System RXYZCM16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolysis is seen as a general increase in exploratory activity in the lighted area. An increase in exploratory activity is reflected by increased latency (the time for the mouse to move to the dark chamber when first placed in the center of the lighted area), increased shuttle activity, increased or unaltered locomotor activity (number of grid lines crossed) and decreased time spent in the dark compartment.

Compounds of Formula I exhibit anxiolytic activity in this assay.

EXAMPLE 14

The Mouse Light/Dark Withdrawal Anxiety Test

The following procedure describes a method to determine whether compounds of Formula I effect the anxiety that occurs after abruptly ceasing chronic treatment with drugs of abuse.

Naive male BKW mice (25–30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 12). Anxiolysis is seen as a general increase in exploratory activity in the lighted area. An increase in exploratory activity is relected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with alcohol (8.0% w/v in drinking water), nicotine (0.1 mg/kg, i.p., twice daily) or cocaine (1.0 mg/kg, i.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawl phase by intraperitoneal injection. Responses are represented as inhibition of the decrease in anxiolytic behavior after the alcohol, cocaine or nicotine treatment is ceased.

EXAMPLE 15

The Mouse Habituation/Cognitive Enhancement Test

The following describes a model to determine the cognitive enhancing effects of compounds of Formula I.

Young adult and aged BKW mice are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 12). Mice are exposed to the two-compartment test area over a 3 day period. The young mice habituate to the test area by day 3 and spend less time exploring the lighted area, whereas exploratory activity in the lighted area remains constant through day 3 for the aged mice. Exploratory activity is seen as latency (the time for the mouse to move to the dark chamber when first placed in the center of the lighted area), locomotor activity (number of grid lines crossed), number of rears and time spent in the lighted compartment. Vehicle or test compounds are administered to the aged mice by intraperitoneal injection. Cognitive enhancing effects in the aged rats are reflected by a decrease in exploratory activity by day 3.

We claim:

1. A compound of formula I

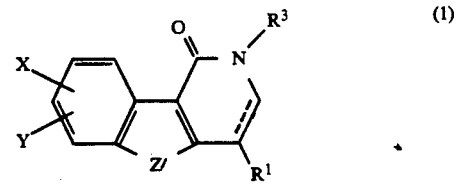

in which:
the dashed line denotes an optional bond;
X and Y are independently selected from hydrogen, halogen, hydroxy, lower alkoxy, lower alkyl, nitro, amino, amino-carbonyl, (lower alkyl)amino, di(-lower alkyl)amino, and (lower alkanoyl)amino;
Z is $-O-$, $-S-$ or $-N(R^2)-$;
$R^1$ and $R^2$ are independently selected from hydrogen and lower alkyl or are together $-(CH_2)_n-$ wherein n is an integer from 2 to 4; except that if Z is $-N(R^2)-$ and $R^2$ is hydrogen or lower alkyl, then the optional bond is present; and R³ is selected from

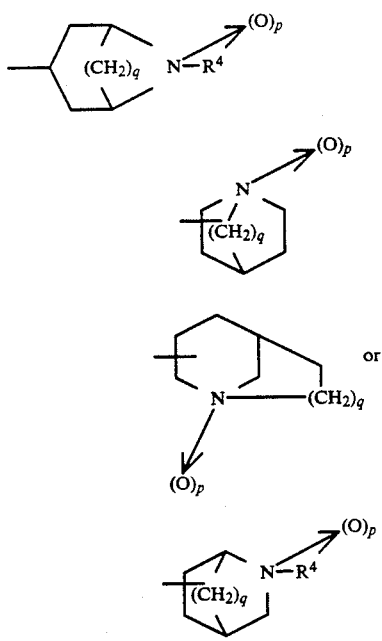

in which:
p is 0 or 1;
q is 1, 2 or 3; and
R⁴ is C$_{1-7}$ alkyl, C$_{3-8}$ cycloalkyl, C$_{3-8}$ cycloalkyl-C$_{1-2}$ alkyl, or a group (CH$_2$)$_t$R⁵ where t is 1 or 2 and R⁵ is thienyl, pyrrolyl, or furyl, each optionally further substituted by one or two substituents selected from C$_{1-6}$ alkyl, C$_{1-6}$ alkoxy, trifluoromethyl or halogen, or is phenyl optionally substituted by one or two substituents selected from C$_{1-4}$ alkoxy, trifluoromethyl, halogen, nitro, carboxy, esterified carboxy, and C$_{1-4}$ alkyl optionally substituted by hydroxy, C$_{1-4}$ alkoxy, carboxy, esterified carboxy or in vivo hydrolyzable acyloxy; or a pharmaceutically acceptable salt, or an individual isomer or mixtures of isomers thereof.

2. A compound of Claim 1 wherein X and Y are independently selected from hydrogen and hydroxy and p is 0.

3. A compound of Claim 2 wherein Z is —N(R²)—.

4. A compound of Claim 3 wherein R³ is 1-azabicyclo[2.2.2]oct-3-yl or 1-azabicyclo[2.2.2]oct-4-yl.

5. A compound of Claim 4 wherein the optional bond is present.

6. A compound of Claim 5 wherein R¹ is hydrogen and R² is methyl.

7. The compound of Claim 6 wherein each X and Y is hydrogen and R³ is 1-azabicyclo[2.2.2]oct-3-yl, namely 2-(1-azabicyclo[2.2.2]oct-3-yl)-1,2-dihydro-5-methyl-1-oxopyrido[4,3-b]indole or a pharmaceutically acceptable salt thereof.

8. The compound of Claim 7 which is (S)-2-(1-azabicyclo[2.2.2]oct-3-yl)-1,2-dihydro-5-methyl-1-oxopyrido[4,3-b]indole or a pharmaceutically acceptable salt thereof.

9. The compound of Claim 8 which is (S)-2-(1-azabicyclo[2.2.2]oct-3-yl)-1,2-dihydro-5-methyl-1-oxopyrido[4,3-b]indole hydrochloride.

10. The compound of Claim 7 which is (R)-2-(1-azabicyclo[2.2.2]oct-3-yl)-1,2-dihydro-5-methyl-1-oxopyrido[4,3-b]indole or a pharmaceutically acceptable salt thereof.

11. The compound of Claim 10 which is (R)-2-(1-azabicyclo[2.2.2]oct-3-yl)-1,2-dihydro-5-methyl-1-oxopyrido[4,3-b]indole hydrochloride.

12. The compound of Claim 6 wherein X is hydroxy in the 8-position, Y is hydrogen and R³ is 1-azabicyclo[2.2.2]oct-3-yl, namely 2-(1-azabicyclo[2.2.2]oct-3-yl)-1,2-dihydro-8-hydroxy-5-methyl-1-oxopyrido[4,3-b]indole or a pharmaceutically acceptable salt thereof.

13. The compound of Claim 12 which is (S)-2-(1-azabicyclo[2.2.2]oct-3-y-1)-1,2-dihydro-8-hydroxy-5-methyl-1-oxopyrido[4,3-b]indole or a pharmaceutically acceptable salt thereof.

14. The compound of Claim 13 which is (S)-2-(1-azabicyclo[2.2.2]oct-3-yl)-1,2-dihydro-8-hydroxy-5-methyl-1-oxopyrido[4,3-b]indole hydrochloride.

15. The compound of Claim 12 which is (R)-2-(1-azabicyclo[2.2.2]oct-3-yl)-1,2-dihydro-8-hydroxy-5-methyl-1-oxopyrido[4,3-b]indole or a pharmaceutically acceptable salt thereof.

16. The compound of Claim 15 which is (R)-2-(1-azabicyclo[2.2.2]oct-3-yl)-1,2-dihydro-8-hydroxy-5-methyl-1-oxopyrido[4,3-b]indole hydrochloride.

17. The compound of Claim 6 wherein each X and Y is hydrogen and R³ is endo-1-azabicyclo[3.3.1]non-4-yl, namely 2-[(endo-1-azabicyclo[3.3.1]non-4-yl)-1,2-dihydro-5-methyl-1-oxopyrido[4,3-b]indole or a pharmaceutically acceptable salt thereof.

18. The compound of Claim 17 which is (S)-2-[(endo-1-azabicyclo[3.3.1]non-4-yl)-1,2-dihydro-5-methyl-1-oxopyrido[4,3-b]indole or a pharmaceutically acceptable salt thereof.

19. The compound of Claim 18 which is (S)-2-[(endo-1-azabicyclo[3.3.1]non-4-yl)-1,2-dihydro-5-methyl-1-oxopyrido[4,3-b]indole hydrochloride.

20. The compound of Claim 17 which is (R)-2-[(endo-1-azabicyclo[3.3.1]non-4-yl)-1,2-dihydro-5-methyl-1-oxopyrido[4,3-b]indole or a pharmaceutically acceptable salt thereof.

21. The compound of Claim 20 which is (R)-2-[(endo-1-azabicyclo[3.3.1]non-4-yl)-1,2-dihydro-5-methyl-1-oxopyrido[4,3-b]indole hydrochloride.

22. The compound of Claim 6 wherein each X and Y is hydrogen and R³ is (endo-9-methyl-9-azabicyclo[3.3.1]non-3-yl, namely 3-[(endo-9-methyl-9-azabicyclo[3.3.1]non-3-yl)-1,2-dihydro-5-methyl-1-oxopyrido[4,3-b]indole or a pharmaceutically acceptable salt thereof.

23. The compound of Claim 22 which is 3-[(endo-9-methyl-9-azabicyclo[3.3.1]non-3-yl)-1,2-dihydro-5-methyl-1-oxopyrido[4,3-b]indole hydrochloride.

24. A compound of Claim 5 wherein R¹ and R² are together —(CH$_2$)$_3$—.

25. The compound of Claim 24 wherein each X and Y is hydrogen and R³ is 1-azabicyclo[2.2.2]oct-3-yl, namely 2-(1-azabicyclo[2.2.2]oct-3-yl)-2,4,5,6-tetrahydro-1-oxo-1H-indolo[3,2,1-ij][1,6]naphthyridine or a pharmaceutically acceptable salt thereof.

26. The compound of Claim 25 which is (S)-2-(1-azabicyclo[2.2.2]oct-3-yl)-2,4,5,6-tetrahydro-1-oxo-1H-indolo[3,2,1-ij][1,6]naphthyridine or a pharmaceutically acceptable salt thereof.

27. The compound of Claim 26 which is (S)-2-(1-azabicyclo[2.2.2]oct-3-yl)-2,4,5,6-tetrahydro-1-oxo-1H-indolo[3,2,1-ij][1,6]naphthyridine hydrochoride.

28. The compound of Claim 5 which is (R)-2-(1-azabicyclo[2.2.2]oct-3-yl)-2,4,5,6-tetrahydro-1-oxo-1H-indolo[3,2,1-ij][1,6]naphthyridine or a pharmaceutically acceptable salt thereof.

29. The compound of Claim 28 which is (R)-2-(1-azabicyclo[2.2.2]oct-3-yl)-2,4,5,6-tetrahydro-1-oxo-1H-indolo[3,2,1-ij][1,6]naphthyridine hydrochoride.

30. A compound of claim 2 wherein Z is —S— or —O—.

31. A compound of claim 30 wherein $R^3$ is 1-azabicyclo[2.2.2]oct-3yl or 1-azabicyclo[2.2.2]oct-4-yl.

32. A compound of claim 31 wherein the optional bond is present.

33. The compound of Claim 32 wherein each X and Y is hydrogen, Z is —S—, $R^1$ is hydrogen and $R^3$ is 1-azabicyclo[2.2.2]oct-3-yl, namely 2-[(1-azabicyclo[2.2.2]oct-3-yl)-1,2-dihydro-1-oxopyrido[4,3-b]benzothiophene or a pharmaceutically acceptable salt thereof.

34. The compound of claim 33 which is (R)-2-[(1-azabicyclo[2.2.2]oct-3-yl)-1,2-dihydro-1-oxopyrido[4,3-b]benzothiophene or a pharmaceutically acceptable salt thereof.

35. The compound of Claim 34 which is (R)-2-[(1-azabicyclo[2.2.2]oct-3-Yl)-1,2-dihydro-1-oxopyrido[4,3-b]benzothiophene hydrochloride.

36. The compound of Claim 33 which is (S)-2-[(1-azabicyclo[2.2.2]oct-3-yl)-1,2-dihydro-1-oxopyrido[4,3-b]benzothiophene or a pharmaceutically acceptable salt thereof.

37. The compound of Claim 36 which is (S)-2-[(1-azabicyclo[2.2.2]oct-3-yl)-1,2-dihydro-1-oxopyrido[4,3-b]benzothiophene hydrochloride.

38. The compound of Claim 32 wherein each X and Y is hydrogen, Z is —O—, $R^1$ is hydrogen and $R^3$ is 1-azabicyclo[2.2.2]oct-3-yl, namely 2-[(1-azabicyclo[2.2.2]oct-3-yl)-1,2-dihydro-1-oxopyrido[4,3-b]benzofuran or a pharmaceutically acceptable salt thereof.

39. The Compound of Claim 38 which is (R)-2-[(1-azabicyclo[2.2.2]oct-3-yl)-1,2-dihydro-1-oxopyrido[4,3-b]benzofuran or a pharmaceutically acceptable salt thereof.

40. The compound of Claim 39 which is (R)-2-[(1-azabicyclo[2.2.2]oct-3-yl)-1,2-dihydro-1-oxopyrido[4,3-b]benzofuran hydrochloride.

41. The compound of Claim 38 which is (S)-2-[(1-azabicyclo[2.2.2]oct-3-yl)-1,2-dihydro-1-oxopyrido[4,3-b]benzofuran or a pharmaceutically acceptable salt thereof.

42. The compound of Claim 41 which is (S)-2-[(1-azabicyclo[2.2.2]oct-3-yl)-1,2-dihydro-1-oxopyrido[4,3-b]benzofuran hydrochloride.

43. A pharmaceutical composition comprising a therapeutically effective amount of a compound of Claim 1 in combination with a pharmaceutically acceptable excipient.

* * * * *